US011696929B2

(12) United States Patent
Athanasiou et al.

(10) Patent No.: US 11,696,929 B2
(45) Date of Patent: Jul. 11, 2023

(54) METHODS AND SYSTEMS FOR CONSERVING HIGHLY EXPANDED CELLS

(71) Applicant: The Regents of the University of California, Oakland, CA (US)

(72) Inventors: Kyriacos A. Athanasiou, Irvine, CA (US); Jerry C. Hu, Irvine, CA (US); Heenam Kwon, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 205 days.

(21) Appl. No.: 16/136,894

(22) Filed: Sep. 20, 2018

(65) Prior Publication Data
US 2019/0083544 A1 Mar. 21, 2019

Related U.S. Application Data

(60) Provisional application No. 62/561,105, filed on Sep. 20, 2017.

(51) Int. Cl.
*A61K 35/32* (2015.01)
*C12N 5/077* (2010.01)
*C12N 5/00* (2006.01)

(52) U.S. Cl.
CPC ............ *A61K 35/32* (2013.01); *C12N 5/0068* (2013.01); *C12N 5/0655* (2013.01); *C12N 2509/00* (2013.01); *C12N 2509/10* (2013.01); *C12N 2513/00* (2013.01); *C12N 2521/00* (2013.01); *C12N 2527/00* (2013.01)

(58) Field of Classification Search
None
See application file for complete search history.

(56) References Cited

U.S. PATENT DOCUMENTS

| 5,824,015 | A | 10/1998 | Sawyer |
| 6,001,352 | A | 12/1999 | Boyan et al. |
| 6,372,494 | B1 | 4/2002 | Naughton et al. |
| 6,511,958 | B1 | 1/2003 | Atkinson et al. |
| 6,582,960 | B1 | 6/2003 | Martin et al. |
| 6,835,377 | B2 | 12/2004 | Goldberg et al. |
| 6,841,150 | B2 | 1/2005 | Halvorsen |
| 6,949,252 | B2 | 9/2005 | Mizuno et al. |
| 7,141,072 | B2 | 11/2006 | Geistlich et al. |
| 7,273,756 | B2 | 9/2007 | Adkisson et al. |
| 8,529,957 | B2 | 9/2013 | Turzi et al. |
| 8,900,860 | B2 | 12/2014 | Huang |
| 9,598,675 | B2 | 3/2017 | Shim et al. |
| 9,993,504 | B2 | 6/2018 | Keller et al. |
| 2001/0053384 | A1 | 12/2001 | Greenleaf et al. |
| 2004/0127963 | A1 | 7/2004 | Uchida et al. |
| 2005/0147959 | A1 | 7/2005 | Frondoza et al. |
| 2010/0249801 | A1 | 9/2010 | Sengun et al. |
| 2011/0184530 | A1 | 7/2011 | Datta et al. |
| 2016/0346025 | A1 | 12/2016 | Bonutti et al. |
| 2017/0127929 | A1 | 5/2017 | Schutt et al. |
| 2018/0333896 | A1 | 11/2018 | Tapsak et al. |
| 2019/0085292 | A1 | 3/2019 | Athanasiou et al. |
| 2021/0187036 | A1 | 6/2021 | Zheng |

FOREIGN PATENT DOCUMENTS

| EP | 1018987 | B1 | 10/2014 |
| GB | 2395196 | A | 5/2004 |
| WO | WO2016040476 | A1 | 3/2016 |

OTHER PUBLICATIONS

Thermo Fisher Scientific "Growth Factors in Thermo Scientific HyClone Cell Culture Serum" available on company's webpage, Application Note: S0801, copyright 2007 (Year: 2007).*
Blain EJ, Gilbert SJ, Hayes AJ, Duance VC. Disassembly of the vimentin cytoskeleton disrupts articular cartilage chondrocyte homeostasis. Matrix Biol. Sep. 2006;25(7):398-408. Epub Jun. 18, 2006.
Capín-Gutiérrez N, Talamás-Rohana P, González-Robles A, Lavalle-Montalvo C, Kourí JB. Cytoskeleton disruption in chondrocytes from a rat osteoarthrosic (OA)—induced model: its potential role in OA pathogenesis. Histol Histopathol. Oct. 2004;19(4):1125-32. doi: 10.14670/HH-19.1125.
Duan W, Wei L, Zhang J, Hao Y, Li C, Li H, Li Q, Zhang Q, Chen W, Wei X. Alteration of viscoelastic properties is associated with a change in cytoskeleton components of ageing chondrocytes from rabbit knee articular cartilage. Mol Cell Biomech. Dec. 2011; 8(4):253-74.
Duan W, Wei L, Cao X, Guo H, Wang L, Hao Y, Wei X. Effect of the disruption of three cytoskeleton components on chondrocyte metabolism in rabbit knee cartilage Chin Med J (Engl). 2014;127(21):3764-70. PMID: 25382333.
Guilak F. The deformation behavior and viscoelastic properties of chondrocytes in articular cartilage. Biorheology. 2000;37(1-2):27-44.
Kerrigan MJ, Hall AC. Stimulation of regulatory volume decrease (RVD) by isolated bovine articular chondrocytes following F-actin disruption using latrunculin B. Biorheology 2005;42(4):283-93. Abstract.
Nofal GA, Knudson CB. Latrunculin and cytochalasin decrease chondrocyte matrix retention. J. Histochem Cytochem. Oct. 2002;50(10):1313-24.
Rottmar M, Mhanna R, Guimond-Lischer S, Vogel V, Zenobi-Wong M, Maniura-Weber K. Interference with the contractile machinery of the fibroblastic chondrocyte cytoskeleton induces re-expression of the cartilage phenotype through involvement of PI3K, PKC and MAPKs. Exp Cell Res. Jan. 15, 2014;320(2):175-87. doi: 10.1016/j.yexcr.2013.11.004. Epub Nov. 15, 2013. PMID:24246223.

(Continued)

*Primary Examiner* — Emily A Cordas
(74) *Attorney, Agent, or Firm* — Nguyen Tarbet LLC

(57) ABSTRACT

The methods described herein are for conserving highly expanded cells that have functional properties such as potential for use in neotissue constructs. For example, highly expanded chondrocytes that can be used to construct neocartilage exhibiting functional properties similar to native articular cartilage. The methods and systems feature processes that form functional, human cartilage using cells that have been expanded to at least $1.5 \times 10^5$ times or P3 or greater. This enables a large quantity of engineered cartilage implants to be produced from few cells.

20 Claims, 15 Drawing Sheets
(11 of 15 Drawing Sheet(s) Filed in Color)

(56) References Cited

OTHER PUBLICATIONS

Smith RL, Trindade MC, Ikenoue T, Mohtai M, Das P, Carter DR, Goodman SB, Schurman DJ. Effects of shear stress on articular chondrocyte metabolism. Biorheology. 2000;37(1-2):95-107.

Smith RL, Carter DR, Schurman DJ. Pressure and shear differentially alter human articular chondrocyte metabolism: a review. Clin Orthop Relat Res. Oct. 2004;(427 Suppl):S89-95.

Takigawa M, Takano T, Shirai E, Suzuki F. Cytoskeleton and differentiation: effects of cytochalasin B and colchicine on expression of the differentiated phenotype of rabbit costal chondrocytes in culture. Cell Differ. Aug. 1984;14(3):197-204.

Murphy et al. TGF-b1, GDF-5, and BMP-2 Stimulation Induces Chondrogenesis in Expanded Human Articular Chondrocytes and Marrow-Derived Stromal Cells. Stem Cells 2015;33:762-773.

Bernstein et al. Tissue Engineering Auricular Cartilage Using Late Passage Human Auricular Chondrocytes. Annals of Plastic Surgery. vol. 80, Supplement 4, Apr. 2018.

Blanco et al. Differentiation-dependent effects of IL-1 and proliferation are related to inducible nitric TGF-beta on human articular chondrocyte. J Immunol 1995; 154:4018-4026.

Caron et al. Redifferentiation of dedifferentiated human articular chondrocytes: comparison of 2D and 3D cultures. Osteoarthritis and Cartilage 20 (2012) 1170-1178.

Chapman et al. Therapeutic Benefit for Late, but Not Early, Passage Mesenchymal Stem Cells on Pain Behaviour in an Animal Model of Osteoarthritis. Stem Cells International, vol. 2017, Article ID 2905104, 11 pages.

Dell'Accio et al. Microenvironment and phenotypic stability specify tissue formation by human articular cartilage-derived cells in vivo. Experimental Cell Research 287 (2003) 16-27.

Giannoni et al. Autologous chondrocyte implantation (ACI) for aged patients: development of the proper cell expansion conditions for possible therapeutic applications. OsteoArthritis and Cartilage (2005) 13, 589-600.

Hsieh-Bonassera et al. Expansion and Redifferentiation of Chondrocytes from Osteoarthritic Cartilage: Cells for Human Cartilage Tissue Engineering. Tissue Engineering: Part A vol. 15, No. 11, 2009.

Huang et al. Cell-based tissue engineering strategies used in the clinical repair of articular cartilage. Biomaterials. Aug. 2016 ; 98: 1-22.

Huang et al. Effects of passage number and post-expansion aggregate culture on tissue engineered, self-assembled neocartilage. Acta Biomater. Oct. 1, 2016; 43: 150-159.

Ko et al. Down-Regulation of Transglutaminase 2 Stimulates Redifferentiation of Dedifferentiated Chondrocytes through Enhancing Glucose Metabolism. Int. J. Mol. Sci. 2017, 18, 2359.

Kudva et al. Initiating human articular chondrocyte re-differentiation in a 3D system after 2D expansion. J Mater Sci: Mater Med (2017) 28:156.

Ma et al. Gene expression profiling of dedifferentiated human articular chondrocytes in monolayer culture. Osteoarthritis and Cartilage 21 (2013) 599-603.

Makris et al. Combined use of chondroitinase-ABC, TGF-β1 and collagen crosslinking agent lysyl oxidase to engineer functional neotissues for fibrocartilage repair. Biomaterials. Aug. 2014 ; 35(25): 6787-6796.

Murphy et al. TGF-b1, GDF-5, and BMP-2 Stimulation Induces Chondrogenesis in Expanded Human Articular Chondrocytes and Marrow-Derived Stromal Cells. Stem Cells 2014;33:762-773.

Murphy et al. Enhancing Post-Expansion Chondrogenic Potential of Costochondral Cells in Self-Assembled Neocartilage. PLOS ONE, Feb. 2013, vol. 8, Issue 2, e56983.

Tan et al. Passage-Dependent Relationship between Mesenchymal Stem Cell Mobilization and Chondrogenic Potential. Osteoarthritis Cartilage. Feb. 2015 ; 23(2): 319-327.

Wang et al. Trophic Stimulation of Articular Chondrocytes by Late-Passage Mesenchymal Stem Cells in Coculture. Journal of Orthopaedic Research, Dec. 2013.

Blain et al. Disassembly of the vimentin cytoskeleton disrupts articular cartilage chondrocyte homeostasis. Matrix Biol. Sep. 2006;25(7):398-408. Epub Jun. 18, 2006.

Brown et al. Ammonium-Chloride-Potassium Lysing Buffer Treatment of Fully Differentiated Cells Increases Cell Purity and Resulting Neotissue Functional Properties. Tissue Engineering: Part C vol. 22, No. 9, 2016.

Capín-Gutiérrez et al. Cytoskeleton disruption in chondrocytes from a rat osteoarthrosic (OA)—induced model: its potential role in OA pathogenesis. Histol Histopathol. Oct. 2004;19(4):1125-32. doi: 10.14670/HH-19.1125.

Choi et al. Fetal Cartilage-Derived Cells Have Stem Cell Properties and Are a Highly Potent Cell Source for Cartilage Regeneration. Cell Transplantation, vol. 25, pp. 449-461, 2016.

Duan et al. Alteration of viscoelastic properties is associated with a change in cytoskeleton components of ageing chondrocytes from rabbit knee articular cartilage. Mol Cell Biomech. Dec. 2011; 8(4):253-74.

Wangping et al. Effect of the disruption of three cytoskeleton components on chondrocyte metabolism in rabbit knee cartilage. Chin Med J (Engl). 2014;127(21):3764-70. PMID: 25382333.

Guilak et al. The deformation behavior and viscoelastic properties of chondrocytes in articular cartilage. Biorheology. 2000;37(1-2):27-44.

Kerrigan et al. Stimulation of regulatory volume decrease (RVD) by isolated bovine articular chondrocytes following F-actin disruption using latrunculin B. Biorheology. 2005;42(4):283-93.

Nofal et al. Latrunculin and cytochalasin decrease chondrocyte matrix retention. J. Histochem Cytochem. Oct. 2002;50(10):1313-24.

Rottmar et al. Interference with the contractile machinery of the fibroblastic chondrocyte cytoskeleton induces re-expression of the cartilage phenotype through involvement of PI3K, PKC and MAPKs. Exp Cell Res. Jan. 15, 2014;320 (2):175-87. doi: 10.1016/j.yexcr. 2013.11.004. Epub Nov. 15, 2013. PMID:24246223.

Smith et al. Effects of shear stress on articular chondrocyte metabolism. Biorheology. 2000;37(1-2):95-107.

Smith et al. Pressure and shear differentially alter human articular chondrocyte metabolism: a review. Clin Orthop Relat Res. Oct. 2004;(427 Suppl):S89-95.

Takigawa et al. Cytoskeleton and differentiation: effects of cytochalasin B and colchicine on expression of the differentiated phenotype of rabbit costal chondrocytes in culture. Cell Differ. Aug. 1984;14(3):197-204.

Trickey et al. The role of the cytoskeleton in the viscoelastic properties of human articular chondrocytes. Journal of Orthopaedic Research 22 (2004) 131-139.

Yourek et al. Cytoskeletal Changes of Mesenchymal Stem Cells During Differentiation. ASAIO J. 2007 ; 53(2): 219-228.

Zanetti et al. Induction of Chondrogenesis in Limb Mesenchymal Cultures by Disruption of the Actin Cytoskeleton. The Journal of Cell Biology. vol. 99 Jul. 1984 115-123.

Takebe et al. "Regulation of p38 MAPK phosphorylation inhibits chondrocyte apoptosis in response to heat stress or mechanical stress." International journal of molecular medicine 27.3 (2011): 329-335.

Loening et al. "Injurious mechanical compression of bovine articular cartilage induces chondrocyte apoptosis." Archives of biochemistry and biophysics 381.2 (2000): 205-212.

Kong et al. "Static mechanical stress induces apoptosis in rat endplate chondrocytes through MAPK and mitochondria-dependent caspase activation signaling pathways." PloS one 8.7 (2013): e69403.

Amirkhani et al. "A rapid sonication based method for preparation of stromal vascular fraction and mesenchymal stem cells from fat tissue." BioImpacts: BI 6.2 (2016): 99.

Goldberg, Stanley. "Mechanical/physical methods of cell distribution and tissue homogenization." Proteomic Profiling. Humana Press, New York, NY, 2015. 1-20.

Kim et al. "The effect of antiseptics on adipose-derived stem cells." Plastic and reconstructive surgery 139.3 (2017): 625.

Jeon et al. "Dynamic compression improves biosynthesis of human zonal chondrocytes from osteoarthritis patients." Osteoarthritis and Cartilage 20.8 (2012): 906-915.

(56) References Cited

OTHER PUBLICATIONS

Stoddart et al. "Enhanced matrix synthesis in de novo, scaffold free cartilage-like tissue subjected to compression and shear." Biotechnology and bioengineering 95.6 (2006): 1043-1051.
Scientific, Thermo. "Growth factors in thermo scientific hyclone cell culture serum." Application Note (2007) 2 pages.
Saadeh et al. "Human cartilage engineering: chondrocyte extraction, proliferation, and characterization for construct development." Annals of plastic surgery 42.5 (1999): 509-513.

* cited by examiner

FIG. 3

| Passage | Cell seeding density (cells/cm$^2$) | Final cell density (cells/cm$^2$) | Cumulative expansion factor | Cumulative cell doubling number |
|---|---|---|---|---|
| P0 -> P1 | 25,000 | 137,667 | 6 | 2.5 |
| P1 -> P2 | 25,000 | 117,778 | 26 | 4.7 |
| P2 -> P3 | 25,000 | 143,111 | 148 | 7.2 |
| P2 -> P3 | 25,000 | 143,807 | 149 | 7.2 |
| P3 -> P4 | 25,000 | 113,422 | 677 | 9.4 |
| P4 -> P5 | 25,000 | 132,222 | 3,581 | 11.8 |
| P4 -> P5 | 25,000 | 117,926 | 3,194 | 11.6 |
| P5 -> P6 | 25,000 | 132,800 | 16,964 | 14.1 |
| P6 -> P7 | 25,000 | 94,044 | 63,816 | 16.0 |
| P6 -> P7 | 25,000 | 109,333 | 74,191 | 16.2 |
| P7 -> P8 | 25,000 | 137,476 | 407,979 | 18.6 |
| P8 -> P9 | 25,000 | 94,222 | 1,537,625 | 20.6 |

FIG. 11

| Passage | Cell seeding density (cells/cm2) | Final cell density (cells/cm2) | Expansion factor/passage | Cumulative expansion factor | Cumulative cell doubling number |
|---|---|---|---|---|---|
| P0 -> P1 | 25,000 | 143,333 | 5.73 | 6 | 2.5 |
| P1 -> P2 | 25,000 | 100,889 | 4.04 | 23 | 4.5 |
| P2 -> P3 | 25,000 | 143,111 | 5.72 | 132 | 7.1 |
| P2 -> P3 | 25,000 | 129,185 | 5.17 | 120 | 6.9 |
| P3 -> P4 | 25,000 | 111,289 | 4.45 | 532 | 9.1 |
| P4 -> P5 | 25,000 | 144,593 | 5.78 | 3,078 | 11.6 |
| P5 -> P6 | 25,000 | 144,000 | 5.76 | 17,731 | 14.1 |
| P6 -> P7 | 25,000 | 96,889 | 3.88 | 68,716 | 16.1 |
| P6 -> P7 | 25,000 | 126,222 | 5.05 | 89,520 | 16.4 |
| P7 -> P8 | 25,000 | 135,111 | 5.40 | 483,805 | 18.9 |
| P8 -> P9 | 25,000 | 64,583 | 2.58 | 1,249,830 | 20.3 |
| P9 -> P10 | 25,000 | 63,929 | 2.56 | 3,196,009 | 21.6 |
| P10 -> P11 | 25,000 | 98,667 | 3.95 | 12,613,583 | 23.6 |

METHODS AND SYSTEMS FOR CONSERVING HIGHLY EXPANDED CELLS

CROSS REFERENCE

This application claims priority to U.S. Provisional Patent Application No. 62/561,105 filed Sep. 20, 2017, the specification(s) of which is/are incorporated herein in their entirety by reference.

GOVERNMENT SUPPORT

This invention was made with government support under Grant No. R01AR067821 awarded by NIH. The government has certain rights in the invention.

FIELD OF THE INVENTION

The present invention relates to cell passaging [e.g., conservative chondrogenic passaging, (CCP)] and rejuvenating, more particularly to methods for passaging cells that result in highly expanded and functional cells such as functional chondrocytes for neocartilage production. The present invention is not limited to chondrocytes or neocartilage constructs.

BACKGROUND OF THE INVENTION

Human articular chondrocytes (hACs) are an autologous cell source used clinically to repair cartilage lesions. In addition to current surgical approaches, including chondroplasty, microfracture, mosaicplasty, and autologous chondrocyte implantation (ACI), a variety of tissue-engineered cartilage products derived from minimally expanded hACs (e.g., from Passages 1-3; P1-P3) has been introduced for clinical use. However, the limited cellularity in cartilage requires extensive passaging (e.g., beyond P3) to obtain sufficient cells for cell-based therapeutics. In addition, chondrocytes are prone to lose their chondrogenic phenotype during monolayer expansion, which impedes successful uses of hACs in tissue engineering applications. Strategies to retain chondrogenic potential of passaged hACs [e.g., conservative chondrogenic passaging; (CCP)] are necessary to advance their use for clinical products for cartilage repair and regeneration.

The effects of cell passaging on the phenotype changes of articular chondrocytes are well-known. Monolayer expansion of chondrocytes results in rapid de-differentiation, elevating type I collagen expression and increasing cell size toward a fibroblastic morphology. Moreover, cells from extensive cell passaging (e.g., Passage 5-8; P5-8) were not able to be restored and generate any cartilage-specific markers, and the expression of cartilage-specific matrix proteins such as aggrecan and type II collagen decrease in a passage number-dependent manner. While chondrocytes at P1 formed tissues with glycosaminoglycan (GAG) and type II collagen, cells at P5 no longer exhibited the chondrocytic morphology or produced cartilage-specific matrix components (e.g., GAG, type II collagen). Strategies to retain or improve the chondrogenic potential of passaged chondrocytes (e.g., various medium compositions and three-dimensional culture systems) have been introduced to overcome the limits resulting from passaging, but with conflicting and limited success, particularly for human-derived cells. Autologous chondrocytes at up to P3 have been used in tissue engineered cartilage products for completed clinical trials. Despite these endeavors, it is still recognized that phenotypic changes in passaged chondrocytes hamper the clinical use of chondrocytes, particularly when even higher passage numbers are required due to cell scarcity.

The technique of rejuvenation, or culturing cells in three-dimensional aggregates prior to use, has been shown to facilitate the restoration of passaged chondrocytes using CCP. The rejuvenation process applied after CCP, cultured in the presence of transforming growth factor-beta 1 (TGF-β1), bone morphogenetic protein-2 (BMP-2), and growth differentiation factor-5 (GDF-5), either alone or in combination, promoted P2 hACs to express chondrogenic genes, such as Sox9, Aggrecan, and type II collagen. The combined treatment of the three factors led to the greatest upregulation of cartilage matrix genes, resulting in formation of mechanically robust neocartilage. Applied to animal cells, the effect of rejuvenation was also shown to revert leporine chondrocytes at high passages back to a chondrogenic phenotype. The neocartilage formed by P7 leporine chondrocytes following rejuvenation exhibited functional properties that were either similar to or greater than the properties of neocartilage derived from cells at lower passages. This remarkable finding has the potential to improve, significantly, current therapies for cartilage repair with respect to use of autologous chondrocytes at higher passages. However, despite promising results regarding rejuvenation of animal cells, questions remain on whether the efficacy seen for highly passaged animal cells can be replicated using human cells. For human cells, the rejuvenation process has only been shown to be effective at producing functional neocartilage with P2 cells.

The functional properties of tissue-engineered cartilage using minimally-passaged cells can be improved with exogenous stimuli, such as TGF-β1, chondroitinase-ABC (c-ABC), and lysyl oxidase-like 2 (LOXL2) (termed "TCL treatment"). TGF-β1 is a well-known factor to induce chondrogenesis and increase functional properties of engineered neocartilage. c-ABC, an enzyme that degrades GAG (i.e., chondroitin and dermatan sulfate), has emerged as a unique factor to increase collagen content and to enhance tensile properties of tissue-engineered cartilage. LOXL2 acts on lysine and hydroxylysine amino acids to create covalent pyridinoline (PYR) crosslinks between collagen fibers. The exogenous application of LOXL2 yielded a remarkable improvement in tensile properties of engineered neocartilage with increased PYR crosslinking content. Applied in combination with TGF-β1 and c-ABC, engineered bovine neocartilage exhibited enhanced tensile properties and collagen content when compared to individual factors. Further, a combined treatment of TGF-β1, c-ABC, and LOXL2 was more effective in enhancing functional properties of engineered bovine neofibrocartilage when compared to other combinations.

Despite these endeavors for minimally passaged hACs, monolayer expansion of hACs through passaging leads to loss of chondrogenic potential, impeding their use for cartilage repair, particularly when high passage numbers are required due to cell scarcity.

SUMMARY OF THE INVENTION

The present invention features methods and systems to conserve the functional potential of highly expanded cells for cell and tissue engineering.
Surprising Results
It was surprisingly discovered, that multiple-passaged hACs had efficacy for production of neocartilage. Despite the cells being passaged multiple times (e.g., beyond P3) and dissociated one or more times (e.g. two times, three time, etc.) using enzymes (e.g., trypsin; known to cause cell damage to the cell membrane) during conservative chondrogenic passaging (CCP) and rejuvenation, the multiple-passaged and dissociated cartilage cells were found to have conserved functional properties similar to primary cells/minimally-passaged cells and form functional neocartilage. The present invention 1) allows the conservation of multiple-passaged hACs through conservative chondrogenic passaging (CCP) and rejuvenation, 2) produces human neocartilage using these passaged conserved hACs, and 3) augments the effects of the rejuvenation on passaged hACs by introducing a combination of TGF-β1, c-ABC, and LOXL2 (termed "TCL treatment"; chemical treatment). Surprisingly, conservation/rejuvenation, followed by TCL treatment reverted hACs at higher passages to a chondrogenic phenotype, leading to formation of mechanically robust human neocartilage similar to those formed by hACs at lower passages. For example, as described in Example 1, rejuvenation, followed by TCL treatment, conserves chondrogenic phenotype of hACs used at higher passages and leads to formation of mechanically robust human neocartilage similar to that formed by hACs of lower passages.

These results were surprising because results are limited from most prior studies, which used minimally passaged cells (≤P3), chondrogenic medium containing only a single growth factor, or animal cells. For example, enhancement of chondrogenic potential of human cartilage cells was observed in minimally-passaged cells (e.g., passaged up to P2/P3) and rejuvenated in the presence of multiple growth factors or of animal cells passaged up to P3 and using a rejuvenation medium containing only a single growth factor. In addition, biochemical and biomechanical properties were enhanced in neocartilage constructs when P2-P7 expanded animal cells were used and exposed to a rejuvenation medium containing only a single growth factor.

These results were not predicted because prior studies attempting to restore chondrogenic potential using highly-passaged cells have failed. Results from previous studies using highly expanded chondrocytes showed that these chondrocytes in the tissue formed do not exhibit the chondrogenic phenotype and the tissue formed itself does not exhibit cartilaginous tissue characteristics (e.g., biochemical and mechanical properties that are similar to those for native tissue). For example, cartilage formed in vivo using human articular cartilage-derived cells (HACSC) at high passages (e.g., up to 20 population doublings) typically displays fibrous tissue with type I collagen immunoreactivity, indicating that the tissue formed in vivo is not hyaline cartilage tissue. Another example is that late passage (P6, 12 population doublings) human mesenchymal stem cells (hMSCs) did not undergo chondrogenesis in monoculture with chondrogenic stimuli (e.g., TGF-β1) or in co-culture with ACs, despite stimulating GAG accumulation. Although increased type H collagen content in expanded bovine synovium-derived stem cells occurred at P4 compared to P1, GAG content was decreased and electric field cell migration was opposite at P4 compared to P1 despite using a chondrogenic media consisting of TGF-β1, a fibroblast growth factor (FGF), and a platelet-derived growth factor (PDGF) (TFP treatment) and micro-pellet three-dimensional culture. Thus, it is unclear whether or not cells of a certain species, passage, culture condition, or chemical treatment are preferentially more likely to adopt a phenotype favorable for cartilage matrix development.

The effect of combining rejuvenation and TCL treatment on engineering functional neocartilage has not been previously evaluated in either animal- or human-derived ACs at high passages. In addition, the effect of rejuvenation itself on engineering functional cartilage exhibited different characteristics between high passage leporine and human chondrocytes. Importantly, TCL treatment on engineered neofibrocartilage did not alter morphology of tissues formed using animal cells, although, as seen in FIG. 4, the morphology of tissues formed using human cells is significantly altered by TCL treatment. The effect of TCL treatment itself and its potential commercial use has not been reported for human cells, which, as shown in this application, can be different than its effect on animal cells.

Therefore, it is surprising that the present invention produces mechanically robust human neocartilage similar to those formed by hACs at lower passages. The use of the rejuvenating medium conserves the chondrogenic phenotype of highly expanded human cartilage cells, and the tissue generated by these cells is functional (i.e. biochemical and mechanical properties are similar to native values).

The present invention features methods for conserving highly expanded cartilage cells to produce their original characteristics or conserving highly expanded cartilage cells to have characteristics that non-highly expanded cartilage cells possess. That includes, for example, highly expanded chondrocytes (e.g., human articular chondrocytes), having particular function or potential such as the potential to produce neotissue. The expanded cartilage cells (e.g., chondrocytes) can be used to construct neotissue (e.g., neocartilage) that exhibits functional properties similar to native articular cartilage. The methods and systems feature a process (e.g., including CCP, rejuvenation, and chemical treatment such as TCL treatment) that forms functional, human cartilage using cells that have been expanded, e.g., to $12.6 \times 10^6$ times or more, or through 11 passages or more. This enables a large quantity of engineered cartilage implants to be produced from few cells.

The present invention features a method for conserving cartilage cells, expanded to high passages. These methods comprise: 1) expanding the cartilage cells to Passage N=5 (P5) and beyond by culturing the cells in monolayer; 2) subjecting expanded cells to dissociation and a three-dimensional environment; and 3) acquiring conserved cartilage cells by dissociating the cells from the three-dimensional environment.

In some embodiments, the conserved cartilage cells exhibit characteristics similar to or better than characteristics exhibited by cartilage cells at P0 (native state) or at Passage N-X, wherein N is the passage number, X is any integer between 1 and N.

The present invention further features a method for conserving human cartilage cells comprising: 1) conservative chondrogenic passaging (CCP) to Passage N=3 (P3) or greater, by culturing the human cartilage cells in monolayer in a CCP medium comprising one or more of a TGF-β superfamily protein, a fibroblast growth factor, and a mitogen (e.g., platelet-derived growth factor, PDGF; TFP treatment); 2) subjecting the expanded cells to dissociation and a three-dimensional environment in the presence of a rejuvenating medium comprising one or more of TGF-β superfamily protein, a growth differentiation factor, and bone morphogenetic protein; and 3) acquiring conserved cartilage cells by dissociating the cells from the three-dimensional environment.

In some embodiments, the method of CCP and rejuvenating cells can be repeated in different amount of times, orders, and combinations. Non-limiting examples comprise: CCP, CCP, rejuvenation; rejuvenation, CCP, CCP; CCP, rejuvenation, CCP.

The present invention further features a method of forming a tissue derived from cartilage cells, expanded to high passages. The method comprising: 1) expanding the cells to Passage N=5 (P5) and beyond, by culturing the cells in monolayer; 2) subjecting the expanded cells to dissociation and a three-dimensional environment; and 3) forming a three-dimensional tissue using dissociated cells from the three-dimensional environment.

In some embodiments, the tissue formed from restored cartilage cells exhibits characteristics similar or better than characteristics exhibited by tissue formed by cartilage cells at P0 (native state) or at Passage N-X, wherein N is the passage number, X is any integer between 1 and N.

The present invention further features a method of forming a tissue derived from cartilage cells. The method comprises: 1) CCP to Passage N=3 (P3) or beyond, by culturing the cells in monolayer in a CCP medium comprising one or more of a TGF-β superfamily protein, a fibroblast growth factor, and a mitogen; and 2) subjecting the expanded cells to dissociation and a three-dimensional environment in the presence of a rejuvenating medium comprising one or more of TGF-β superfamily protein, a growth differentiation factor, and bone morphogenetic protein; and 3) forming a three-dimensional tissue using dissociated cells from the three-dimensional environment in the presence of chemical treatment for a period of time comprising of one or more TGF-β superfamily proteins, one or more proteoglycan degrading agents, and one or more cross-linking agents.

In some embodiments, the cells in the three-dimensional culture form neocartilage, which has mechanical properties similar to native articular cartilage. Forming the tissue in three-dimensional culture comprises fabricating the tissue with circular, square, rectangular, curved, or customized shapes.

In some embodiments, the resulting tissue can be used to treat chondral lesions, osteochondral lesions, and osteoarthritic conditions.

In appropriate circumstances, the methods of CCP and rejuvenating cells, and forming a tissue can be repeated in different amount of times, orders, and combinations.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which:

FIG. 3 shows CCP metrics at each passage for human articular chondrocytes, derived from a 43 year-old male. Note italicized rows indicate cell expansion from cryogenically stored cells.

FIG. 11 shows CCP metrics of human articular chondrocytes, derived from a 34 year-old male, passaged up to P11. Note italicized rows indicate cell expansion from cryogenically stored cells.

DETAILED DESCRIPTION OF THE INVENTION

The present invention features methods for restoring cartilage cells, expanded to high passages, P3 or greater. For example, highly expanded chondrocytes (e.g., human articular chondrocytes) can be used to construct neotissue (e.g., neocartilage) exhibiting functional properties similar to native articular cartilage. The methods and systems feature a process (e.g., CCP, rejuvenation and TCL treatment) that forms functional, human cartilage using cells that have been expanded, e.g., to 12.6×10 times or more, or through 11 passages or more through conservative chondrogenic passaging (CCP). This enables a large quantity of engineered cartilage implants to be produced from few cells. Note the present invention is not limited to producing highly expanded chondrocytes or producing cells for human cartilage production. The present invention is also not limited to the number of passages described herein.

Figure 1:
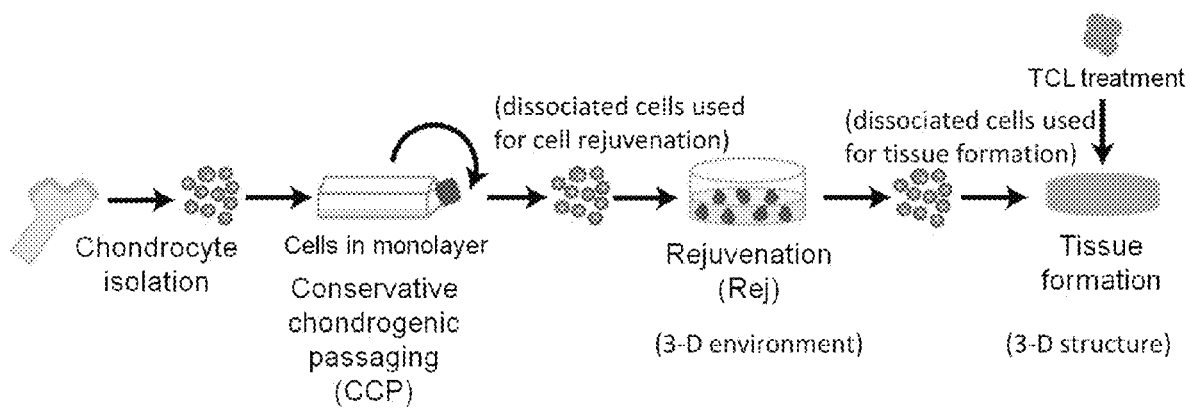
FIG. 1 shows a schematic diagram of the process for restoring cartilage cells using conservative chondrogenic passaging (CCP) and rejuvenation (Rej), and for tissue formation using the restored cartilage cells in the presence of chemical treatment such as TCL treatment. Dissociated cells are used for cell rejuvenation and tissue formation.

The methods of the present invention feature a combination of: 1) CCP), 2) rejuvenation, 3) tissue formation using different processes such as the self-assembling process, and 4) agents, including chemical, biophysical, mechanical, such as a regimen of optimized bioactive agents (e.g., TCL treatment) (FIG. 1). Without wishing to limit the present invention to any theory or mechanism, it is possible that the TCL treatment step or rejuvenation may be eliminated; however, the functionality of the produced tissue is reduced as compared to tissue made with the rejuvenation or TCL treatment alone. As non-limiting examples, the methods of the present invention comprise: 1) CCP, rejuvenation, and a self-assembling process; 2) CCP, a self-assembling process, and addition of bioactive agents (e.g., TCL treatment); or 3) CCP, rejuvenation, a self-assembling process, and addition of bioactive agents (e.g., TCL treatment).

In some embodiments, the cartilage cells are human cells and may comprise chondrocytes, fibrochondrocytes, or combination thereof. The chondrocytes are derived from hyaline or elastic cartilage, including but not limited to all diarthrodial joints, ribs, nose, larynx, trachea, ear, and epiglottis. The fibrochondrocytes are derived from, but not limited to temporomandibular joint, intervertebral disc, meniscus, tendon, and ligament.

Conservative Chondrogenic Passaging (CCP)

As a non-limiting example, cells are cultured (for CCP purposes) in monolayer in CCP medium. For appropriate circumstances, the CCP medium comprises one or more of: a TGF-β superfamily protein, an FGF, and a mitogen [e.g., media supplemented with TFP (TGF-β, FGF-2, PDGF, and/or the like, or combinations thereof, etc.] to expand the cells up to P11.

The TGF-β superfamily protein in the CCP medium comprises one or more of but not limited to: TGF-β1; TGF-β2; TGF-β3; TGF-β4; an GDF; an BMP; a glial-derived neurotrophic factor; NODAL, mullerian inhibiting hormone; or a combination thereof. Non-limiting examples of GDF comprise one or more of: GDF-1, GDF-2, GDF-3, GDF-5, GDF-6, GDF-8, GDF-9, GDF-10, GDF-11, GDF-15. Non-limiting examples of BMP comprise one or more of: BMP-1, BMP-2, BMP-3, BMP-4, BMP-5, BMP-6, BMP-7, BMP8, BMP-10, BMP-11, BMP-15, or a combination thereof. Fibroblast growth factor examples comprise but not limited to FGF-1, FGF-2, FGF-3, FGF-4, FGF-5, FGF-6, FGF-7, FGF-8, FGF-9, FGF-10, FGF-11, FGF-12, FGF-13, FGF-14, FGF-16, FGF-17, FGF-18, FGF-19, FGF-20, FGF-21, FGF-22, FGF-23, or a combination thereof. Non-limiting examples of the mitogen comprise PDGF-/PDGF-AA/-BB/-AB, chemical substances triggering mitosis through mitogen-activated protein kinase (MAPK), or a combination thereof.

For appropriate circumstances, the method of CCP comprises subjecting the cells in CCP medium containing epidermal growth factor (EGF), insulin-like growth factors (IGFs), superficial zone protein (SZP)/proteoglycan 4 (PRG4), or a combination thereof. In some embodiments, the method of CCP comprises subjecting the cells in CCP medium containing proteoglycan molecules including, but not limited to aggrecan, hyaluronan, chondroitin-4/-6 sulfate, keratan sulfate, dermatan sulfate, heparin, heparin sulfate etc., or the medium containing collagen molecules including, but not limited to collagen types 1, 2, 3, 4, 5, 6, 9, 10, 11, 12, 14, 16, 22, 27, or a combination thereof.

In some embodiments, the method of CCP comprises subjecting the cells in CCP medium containing matrix degrading enzymes, cytoskeleton modifying reagents, cross-linking agents, or a combination thereof (e.g., TCL treatment). The matrix degrading enzymes comprise one or more of, but not limited to chondroitinase-ABC, trypsins, pepsins, papains, hyaluronidases, heparinases, keratinases, collagenases or a combination thereof. The cytoskeleton modifying reagents comprise one or more of, but not limited to cytochalasins and latrunculins. The cytoskeleton modifying reagents comprise one or more of, but not limited to cytochalasins and latrunculins. The cross-linking agents comprise one or more of, but not limited to a lysyl oxidase protein such as LOXL1 LOXL2, LOXL3, and LOXL4 etc.; other cross-linking enzymes/agents such as genipin, glutaraldehyde, etc; other cross-linking enzymes/agents that yield pyridinoline cross-links, or a combination thereof.

Additional appropriate circumstances for methods of CCP include subjecting the cells to 1) hypoxic conditions or 2) mechanical stimulation. For example, the hypoxic conditions are derived physically or from chemical treatment to reach less than 21% oxygen. The chemical treatment comprises one or more of, but not limited to desferrioxamine, cobalt, glucose oxidase (GOX)/catalase (CAT), or a combination thereof. Mechanical stimulation includes but not limited to fluid induced shear stress, hydrostatic pressure, or a combination thereof.

Conservative chondrogenic passaging for some circumstances involves enzymatic digestion, mechanical dissociation, or a combination thereof. The enzymatic digestion comprises but not limited to subjecting the passaged cells to proteolytic enzymes/matrix degrading enzymes such as trypsins, collagenases, or a combination thereof.

In some embodiments, the monolayer cells are cultured at a seeding density of 500,000 cells/cm$^2$ or less, expanded to 1.5×10$^5$ times or more, and expanded through 2, 3, 4, 5, 6, 7, 8, 9, 10, or 11 passages or more. A non-limiting example comprises cells being cultured at a seeding density of 25,000 cells/cm$^2$ and expanded to at least 1.5×10$^5$ times. Non-limiting examples also comprise expanding to 0.9 million or 1.5 million at P9, 12.6 million at P11.

Rejuvenation

After repeated series of CCP, cells are dissociated from monolayer culture using enzymes into a cell suspension and subjected to three-dimensional environment in the presence of a rejuvenating medium. For example, the cells are cultured (for rejuvenation) in three dimensional suspension (e.g., for one week) in the presence of a rejuvenation treatment before being enzymatically dissociated. The rejuvenation medium comprises one or more of a TGF-β superfamily proteins, a growth differentiation factor (GDF), and a BMP protein (e.g., TGF-β1, GDF-5, and/or BMP-2, and/or the like, or combinations thereof, etc.). Note the present invention is not limited to TGF-β1, GDF-5, and/or BMP-2. In some embodiments, the rejuvenation treatment comprises one or a combination of proteins from the TGF-beta superfamily, e.g., TGF-beta proteins [e.g., TGF-beta1, TGF-beta1, TGF-beta3, TGF-beta4, etc.), GDF (e.g., GDF-1, GDF-2, GDF-3, GDF-5, GDF-6, GDF-8, GDF-9, GDF-10, GDF-11, GDF-15, or combination thereof), BMP (BMP-1, BMP-2, BMP-3, BMP-4, BMP-5, BMP-6, BMP-7, BMP-8, BMP-10, BMP-11, BMP-15, or combination thereof), glial-derived neurotrophic factors, NODAL, and mullerian inhibiting hormone, etc.].

In some embodiments, subjecting the cells to the three-dimensional environment comprises a use of a medium containing epidermal growth factor (EGF), FGF-2, insulin-like growth factors (IGFs), superficial zone protein (SZP)/proteoglycan 4 (PRG4), or a combination thereof. For example, IGF-1 is used as an alternative to the TGF-beta superfamily protein. IGF-1 also may be used in combination with BMP. IGF has been shown to promote chondrocyte proliferation during chondrogenesis and is also involved in promoting the expression of cartilage-specific matrix. Another example of the method features systemic administration of compounds to increase cell viability and proliferation (e.g., EGF and/or FGF-2 and/or the like, or combinations thereof, etc.) in conjunction with the suspension culture.

Subjecting the cells to the three-dimensional environment can also comprise a use of medium containing 1) proteoglycan molecules or 2) matrix degrading enzymes, cytoskeleton modifying reagents, cross-linking agents, or a combination thereof. Proteoglycan molecules comprise, but not limited to aggrecan, hyaluronan, chondroitin-4/-6 sulfate, keratan sulfate, dermatan sulfate, heparin, heparin sulfate etc., or the medium containing collagen molecules including, but not limited to collagen types 1, 2, 3, 4, 5, 6, 9, 10, 11, 12, 14, 16, 22, 27, or a combination thereof. Examples of matrix degrading enzymes comprise one or more of, but not limited to chondroitinase-ABC, trypsins, pepsins, papains, hyaluronidases, heparinases, keratinases, collagenases, or a combination thereof. Non-limiting examples of cytoskeleton modifying reagents comprise one or more of cytochalasins and latrunculins. Examples of cross-linking agents comprise one or more of, but not limited to: a lysyl oxidase protein such as LOXL1, LOXL2, LOXL3, and LOXL4 etc.; other cross-linking enzymes/agents such as genipin, glutaraldehyde, etc.; other cross-linking enzymes/agents that yield pyridinoline cross-links, or a combination thereof.

In appropriate circumstances, culturing in the three-dimensional environment comprises subjecting the cells to 1) hypoxic conditions derived physically or from chemical treatment to reach less than 21% oxygen and/or mechanical stimulation. The chemical treatment comprises one or more of, but not limited to desferrioxamine, cobalt, glucose oxidase (GOX)/catalase (CAT), or a combination thereof.

Examples of mechanical stimulation comprise but not limited to fluid induced shear stress, hydrostatic pressure, or a combination thereof.

In some embodiments, the three-dimensional environment comprises 1) suspension culture at a seeding density of 100,000 cells/ml or more and 2) culturing the passaged cells for rejuvenating is for 1-14 days. A non-limiting example comprises seeding suspension culture at 750,000 cells/ml and culturing for 14 days.

Subjecting cells in the three-dimensional environment also can comprise non-suspension culture, such as scaffold-free or scaffold-based three-dimensional culture, or a combination thereof. Examples of the scaffold-free three-dimensional culture comprise but not limited to self-assembly, pellet culture, micromass, hanging drop method, embryoid bodies, or a combination thereof. Non-limiting examples of the scaffold-based three-dimensional culture comprise gel, beads, sheet, freeze-dried materials, porous scaffolds, or a combination thereof. The composition of scaffolds is derived from natural, synthetic materials, or modified natural materials, but not limited to collagens, silk, chitosan, poly(lactic acid), poly(ethylene glycol), or a combination thereof.

Tissue Formation

In some embodiments, the method further comprises dissociating the three-dimensional cultured cells via 1) enzymatic digestion or 2) mechanical dissociation. Examples of the enzymatic digestion comprise subjecting the cells to proteolytic enzymes/matrix degrading enzymes such as trypsin, collagenase, or a combination thereof. Therefore, the matrices the cells have made up to this point are digested and removed. In some embodiments, the dissociated cells can be used for cell therapies or forming a tissue to treat cartilage defects. A non-limiting example comprises formation of neocartilage that had mechanical properties similar to native articular cartilage.

The suspended cells are then seeded anew in three-dimensional culture to form cartilaginous tissue (for self-assembly process). In some embodiments, the period of time of culturing in the three-dimensional culture is at least 10 days.

In some embodiments, the method of forming a tissue comprises dissociating the three-dimensional cultured cells and seeding the cells in a three-dimensional culture.

A non-limiting example of forming the tissue in three-dimensional culture comprises scaffold-free culture systems, which comprise but not limited to self-assembly, pellet culture (aggregate formation), micromass, hanging drop method, embryoid bodies, or a combination thereof.

In appropriate circumstances, forming a tissue in three-dimensional culture comprises scaffold-based culture systems, which comprise but not limited to gel, beads, sheet, freeze-dried materials, porous scaffolds, or a combination thereof. The composition of scaffold are derived from natural, synthetic materials, or modified natural materials, but not limited to collagens, silk, chitosan, poly(lactic acid), poly(ethylene glycol), or a combination thereof.

In some embodiments, forming a tissue in three-dimensional culture comprises treating the three-dimensional culture of the tissue with a chemical treatment for a period of time. The chemical treatment comprises one or a combination of one or more TGF-β superfamily proteins, one or more proteoglycan degrading agents, and one or more cross-linking agents (TCL treatment). Non-limiting examples of the chemical treatment comprise treating with the TGF-3 superfamily protein for at least 10 days, treating with the proteoglycan degrading agent for at least 30 minutes on any day or days after day 4, and treating with the cross-linking agent for any duration after day 7. A specific example comprises treating the tissue with TGF-β1 throughout the culture, proteoglycan degrading agent for 4 hrs at day 7, and cross-linking agent from day 7 to 21.

Non-limiting examples of the TGF-β superfamily protein comprise one or more of: TGF-β1, TGF-β2, TGF-β3, TGF-β4, an GDF, an BMP, a glial-derived neurotrophic factor, NODAL, mullerian inhibiting hormone, or a combination thereof. Non-limiting examples of GDF comprise one or more of: GDF-1, GDF-2, GDF-3, GDF-5, GDF-6, GDF-8, GDF-9, GDF-10, GDF-11, GDF-15, or a combination thereof. Non-limiting examples of BMP comprise one or more of: BMP-1, BMP-2, BMP-3, BMP-4, BMP-5, BMP-6, BMP-7, BMP8, BMP-10, BMP-11, BMP-15, or a combination thereof. Examples of the proteoglycan degrading agents comprise, but not limited to chondroitinase-ABC, trypsins, pepsins, papains, hyaluronidases, heparinases, keratinases, collagenases, or a combination thereof. Examples of the cross-linking agents comprise, but not limited to a lysyl oxidase protein such as LOXL1 LOXL2, LOXL3, and LOXL4, or other cross-linking enzymes/agents such as genipin, glutaraldehyde, etc.; other cross-linking enzymes/agents that yield pyridinoline cross-links, or a combination thereof.

In some embodiments, forming the tissue in three-dimensional culture comprises subjecting the tissue to other growth factors, including but not limited to EGF, FGF-2, IGF, superficial zone protein (SZP)/proteoglycan 4 (PRG4), or a combination thereof. Forming the tissue in three-dimensional culture also can comprise subjecting the tissues to proteoglycan molecules including, but not limited to aggrecan, hyaluronan, chondroitin-4/-6 sulfate, keratan sulfate, dermatan sulfate, heparin, heparin sulfate etc., or to collagen molecules including, but not limited to collagen types 1, 2, 3, 4, 5, 6, 9, 10, 11, 12, 14, 16, 22, 27, or a combination thereof.

In some embodiments, forming the tissue in three-dimensional culture comprises subjecting the tissue to 1) hypoxic conditions or 2) mechanical stimulation. The hypoxic conditions are derived physically or from chemical treatment to reach less than 21% oxygen. The chemical treatment comprises one or more of, but not limited to desferrioxamine, cobalt, glucose oxidase (GOX)/catalase (CAT), or a combination thereof. Methods of mechanical stimulation comprise but not limited to fluid induced shear stress, compressive stress, tensile stress, hydrostatic pressure or a combination of thereof.

In some embodiments, chemical treatments are applied during culture to obtain the desired tissue qualities (e.g., TCL treatment as described in Example 1). In some embodiments, the cells generated by the procedures described above may be used for generating mechanically stimulated cartilage implants. In some embodiments, the TCL treatment comprises one or a combination of a TGF-beta superfamily protein (TGF-beta1, TGF-beta1, TGF-beta3, TGF-beta4, etc.), chondroitinase-ABC, and/or a lysyl oxidase protein (e.g., LOXL2, LOXL1, LOXL3, LOXL4, etc.). In some embodiments, other proteoglycan degrading enzymes/agents (e.g., trypsin, pepsin, papain, etc.) and cross-linking enzymes/agents (e.g., genipin, etc.) may be used as alternatives for c-ABC and LOXL2, respectively. For alternatives to TGF-beta, other growth factors known to produce extracellular matrix (ECM) can be used such as, for example, other members of TGF-beta superfamily, IGFs, BMPs, etc.

In appropriate circumstances, cells are combined with non-chondrocytic cells (e.g., skin-derived stem cells) to reduce further the number of donor chondrocytes needed.

As previously discussed, the present invention is not limited to cartilage cells. For example, the processing methods described can also be applied to cells derived from osteoarthritic tissues to produce functional cartilage implants. The methods of the present invention may be applied to fibrochondrocytes and/or human adult mesenchymal stem cells (e.g., derived from various locations including but not limited to bone marrow, adipose tissue, and skin) to differentiate into chondrocytes and produce functional cartilage implants.

The present invention further features methods for producing cartilaginous implants derived from human chondrocytes at P2, P3, P4, P5, P6, P7, P8, P9, P10, P11, or more that exhibit functional properties similar to native articular cartilage. The cartilaginous implants may be for replacement of the entire knee (e.g., for numerous patients), e.g., for patients suffering from trauma and/or osteoarthritic disease, etc.

Figure 2:
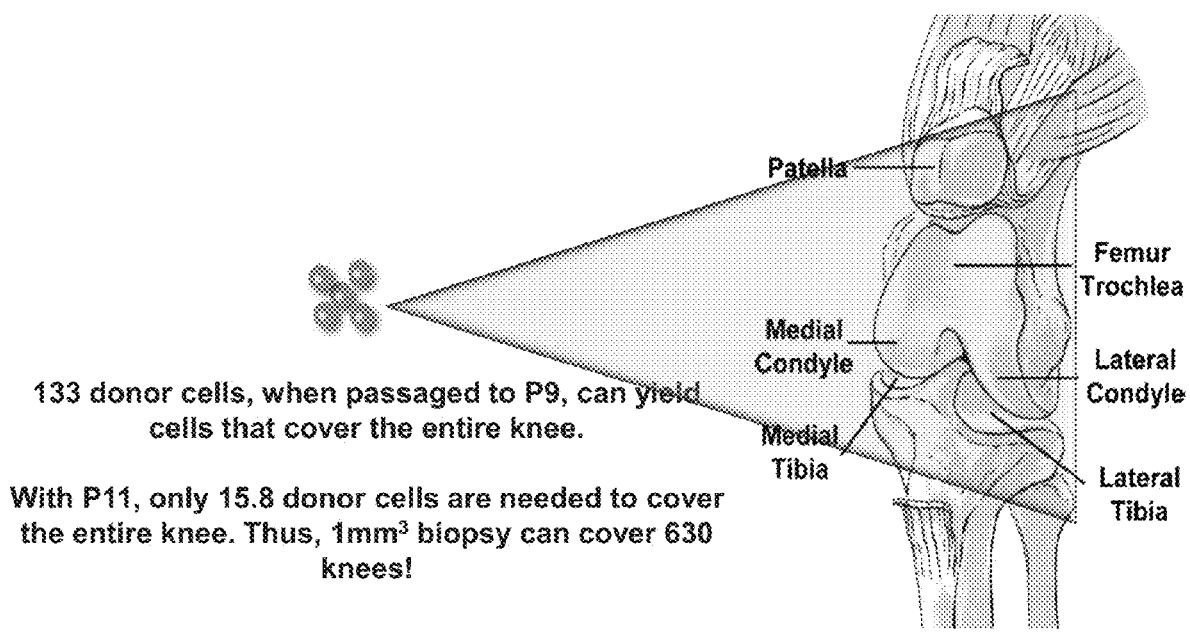
FIG. 2 shows a schematic view of the human knee. According to calculations, with P11, a 1 $mm^3$ biopsy can cover 630 knees.

Calculations have estimated the number of cells that can be generated from donor chondrocytes. A 1 mm$^3$ biopsy provides approximately 10,000 cells (10,000 cells/mm$^3$ biopsy). Using the methods of the present invention, one donor chondrocyte can be expanded to $1.5 \times 10^6$ cells with 9 passages. Thus, a 1 mm$^3$ biopsy can yield $1.5 \times 10^{10}$ cells. Considering the approximate volume of a human knee is 20,000 mm$^3$, and 10,000 cells/mm$^3$ are needed for replacement, the $1.5 \times 10^{10}$ cells of the 1 mm$^3$ biopsy can provide enough coverage for 75 knees. Stated differently, the $1.5 \times 10^{10}$ cells of the 1 mm$^3$ biopsy can cover a volume of $1.5 \times 10^6$ mm$^3$. This could be 1500 different 1,000 mm$^3$ sized repairs. Again, for one knee (see FIG. 2 showing a schematic view of the knee), the number of cells needed for repair would be $2 \times 10^8$ cells (20,000 mm$^3 \times$ 10,000 cells/mm$^3$), and this could be generated by 133 donor cells ($2 \times 10^8$ cells $\div 1.5 \times 10^6$ cells per donor). The 133 donor cells could be obtained from a 0.013 mm$^3$ biopsy (133 cells $\div$ 10,000 cells per mm$^3$ biopsy). With 11 passages, even fewer cells, 15.8 cells are needed to cover one knee, and 1 mm$^3$ biopsy can provide enough coverage for 630 knees.

Table 1 provides a summary of characteristics for cells and tissues produced from the methods featured in the present invention. In some embodiments, the methods produce functional cartilage cells and tissues that have characteristics similar to or better than characteristics exhibited by native state cells (Passage P=0) or at Passage N-X, wherein N is the passage number, X is any integer between 1 and N. For example, when N is 3 and X is 3, then N-X is 0, indicating that the cartilage cells exhibit features similar to native state of P0. As stated above, Passage N-X can produce cartilage cells and tissues that have characteristics better than the P0, native state.

TABLE 1

Conservation Characteristics.

| | Cells | Tissue |
|---|---|---|
| Morphology | Conserved cells exhibit cell morphology similar or better than cell morphology exhibited by cells at P0 (native state) or at Passage N-X, wherein N is the passage number, X is any integer between 1 and N. | Conserved cells exhibit cell morphology similar or better than cell morphology exhibited by cells at P0 (native state) or at Passage N-X, wherein N is the passage number, X is any integer between 10 and N. |
| Extracellular matrix (ECM) expression or production | Conserved cells express GAG and type II collagen levels similar or better than GAG and type II collagen levels expressed by cells at P0 (native state) at Passage N-X, wherein N is the passage number, X is any integer between 1 and N. | Conserved cells produce GAG and type II collagen contents similar or better than GAG and type II collagen contents produced by cells at P0 (native state) or at Passage N-X, wherein N is the passage number, X is any integer between 1 and N. |
| Mechanical Properties | | Conserved cells form tissues that exhibit compressive properties (e.g., relaxation modulus ($E_r$), and instantaneous modulus ($E_i$), compressive aggregate modulus ($H_A$)) and tensile properties (e.g., Young's modulus ($E_Y$), Ultimate Tensile Strength (UTS) similar or better than compressive properties and tensile properties exhibited by the tissues formed by cells at P0 (native state) or at Passage N-X, wherein N is the passage number, X is any integer between 1 and N. |

Note:
N is the passage number, X is any integer between 1 and N. Passage N-X can be below P0, the native state (i.e., conserved cells or a tissue formed by the conserved cells can exhibit one or more characteristics that is better than those exhibited by P0 cells).

The present invention also features a method of fabricating a tissue in three-dimensional culture comprises forming the tissue to integrate into another tissue. Non-limiting examples comprise: 1) integration of cartilage to cartilage; 2) integration of cartilage to bone, and 3) integration of ligament to bone.

The present invention also features a method of conserving cartilage cells, expanded to greater than P1 but limited to P4; these are the passage numbers most commonly used for current therapies. For example, the method comprises CCP by culturing the cells in monolayer in a CCP medium and subjecting the passaged cells to a three-dimensional environment in a rejuvenating medium. In some embodiments, the CCP medium comprises one or more of: a TGF-β superfamily protein, an FGF, and a mitogen and the rejuvenating medium comprises one or more of TGF-β superfamily protein, an GDF, and an BMP.

The present invention also features a method of forming a tissue derived from cartilage cells, expanded to greater than P1 but limited to P4; these are the passage numbers most commonly used for current therapies. For example, the method comprises CCP cells in monolayer in a CCP medium, subjecting the passaged cells to a three-dimensional environment in a rejuvenating medium, and forming a tissue in presence of chemical treatment for a period of time. The CCP medium comprises one or more of: a TGF-β superfamily protein, an FGF, and a mitogen. The rejuvenating medium comprises of one or more of TGF-β superfamily protein, an GDF, and an BMP.

The present invention is not limited to chondrocytes and neocartilage construct production, and the present invention is not limited to the methods and compositions of Example 1 (e.g., the composition of medium for rejuvenation, the composition of TCL treatment of Example 1, etc.). The present invention also is not limited to the number of passages described herein.

These methods also can be utilized in other cell types such as human adult mesenchymal stem cells, human embryonic stem cells, genetically modified cells, or a combination thereof. Human adult mesenchymal stem cells are derived from various locations including but not limited to bone marrow, adipose tissue, and skin. The genetically modified cells comprise induced pluripotent stem cells (iPSCs).

These methods also can be utilized in cell types derived from other tissue types such as musculoskeletal tissues, cardiovascular tissue, neurosensory tissues, and liver tissue.

EXAMPLE 1

It was surprisingly found that CCP and rejuvenation, followed by TCL treatment, reverts hACs at higher passages (≤P3) to a chondrogenic phenotype, leading to formation of mechanically robust human neocartilage similar to those formed by hACs at lower passages.

Example 1 describes the restoration of hACs passaged up to P11 and the efficacy of a combined treatment of TGF-β1 (T), chondroitinase-ABC (C), and lysyl oxidase-like 2 (L) (termed "TCL treatment") on further improving functional properties (e.g., augmenting effects of rejuvenation) of engineered human neocartilage as a function of passage number. The present invention is not limited to the methods, systems, compositions, and treatments described herein.

For reference, hACs are an autologous cell source used clinically to repair cartilage lesions. In addition to current surgical approaches, including chondroplasty, microfracture, mosaicplasty, and autologous chondrocyte implantation (ACI), a variety of tissue-engineered cartilage products derived from expanded hACs has been introduced for clinical use. Limited cellularity in cartilage requires passaging to obtain sufficient cells for cell-based therapeutics. However, chondrocytes are prone to lose their chondrogenic phenotype during monolayer expansion, which impedes successful uses of hACs in tissue engineering applications. For example, monolayer expansion of chondrocytes results in rapid de-differentiation, elevating type I collagen expression and increasing cell size toward a fibroblastic morphology. Moreover, cells from extensive cell passaging (e.g., passage 5-8 or P5-8) alone are currently not able to redifferentiate and generate any cartilage-specific markers. Previous studies showed decreases in expression of cartilage-specific matrix proteins such as aggrecan and type II collagen in a passage number-dependent manner. While chondrocytes at P1 formed tissues with GAG and type II collagen, cells at P5 no longer exhibited the chondrocytic morphology or produced cartilage-specific matrix components.

In Example 1, the scaffold-free, self-assembling process (that generates mechanically robust neocartilage) was used to form human neocartilage using cells from a 43 year-old male. Example 1 describes that CCP and rejuvenation enhanced GAG content and type II collagen staining at all passages and also flattened constructs up to P7 with chondrogenic phenotype present. Addition of TCL treatment extended chondrogenic phenotype to P9. For both P7 and P9 constructs, TCL treatment significantly enhanced GAG content by 4.5-fold and type II collagen staining. Also, TCL treatment resulted in human neocartilage constructs, derived from high passages (e.g., P7 and P9), displaying mechanical properties similar to those derived from low passages (e.g., P3 and P5). The efficacy of CCP, rejuvenation, and TCL treatment on engineering functional neocartilage derived from cells of high passages were also shown using a different donor (a 34 year-old male): human neocartilage derived from P7 and P11 cells exhibited chondrogenic phenotype and mechanical properties similar to neocartilage derived from P3 cells. These data suggest that CCP and rejuvenation followed by TCL treatment may be a viable new strategy to generate functional human neocartilage using extensively passaged cells (e.g., cell doubling number from 4.5 at P2 to 23.6 at P11, see FIG. 11, or higher cell doubling numbers), advancing their clinical use for cartilage repair and regeneration.

Human articular chondrocyte isolation and CCP: Chondrocytes were isolated from human articular cartilage without signs of pathology, derived from a 43 year-old male. For a repeated study, chondrocytes derived from a 34 year-old male were used. Minced cartilage was digested in 0.2% collagenase type II (Worthington, Lakewood, N.J.) solution including 3% fetal bovine serum (FBS, Atlanta Biologicals, Lawrenceville, Ga.) for 18 hrs at 37° C., followed by filtration through a 70 µm strainer. Isolated cells were counted, resuspended in freezing medium consisting of 90% FBS and 10% dimethyl sulfoxide (DMSO), and stored in liquid nitrogen until use. To obtain higher numbers of cells through cell passaging, CCP was applied. Briefly, hACs were seeded at a cell density of 25,000 cells/cm$^2$ and expanded in chemically defined medium (CDM) (DMEM with high glucose/GlutaMAX™, 1% penicillin-streptomycin-fungizone (P/S/F), 1% non-essential amino acids (Gibco), 1% ITS+ premix (BD Biosciences), 50 µg/ml ascorbate-2-phosphate, 40 µg/ml L-proline, 100 µg/ml sodium pyruvate, and 100 nM dexamethasone), supplemented with 2% FBS, 1 ng/ml TGF-β1 (Peprotech, Rocky Hills, N.J.), 5 ng/ml bFGF (Peprotech), and 10 ng/ml PDGF (Peprotech). Cells were passaged using 0.05% trypsin-EDTA (Gibco), followed by 0.2% collagenase type II solution containing 3% FBS, and frozen at P2, P4, P6, and P8 in liquid nitrogen until use. To examine the effects of rejuvenation and TCL, after thawing, cells underwent one more passage, leading to P3, P5, P7, and P9; cells then underwent self-assembly without rejuvenation (Ctrl) or rejuvenation followed by self-assembly (Rej). For the repeated study, cells frozen at P2, P6, and P10 were processed, as described above, to yield self-assembled constructs. The following formulae were used: cell doubling number=log(expansion factor)/log(2); expansion factor=initial cell number/final cell number.

The rejuvenation process: Cells at P3, P5, P7, and P9 were seeded at a cell density of 750,000 cells per ml in 1% agarose-coated plates for rejuvenation and maintained in CDM supplemented with 10 ng/ml TGF-β1, 100 ng/ml GDF-5, and 100 ng/ml BMP-2 for 7 days. After 7 days of culture, aggregates were digested and dissociated using 0.05% trypsin-EDTA, followed by 0.2% collagenase type II solution containing 3% FBS. After filtering, the resulting cells were seeded. For the repeated study, cell rejuvenation at P3, P7, and P11 was performed as above.

Neocartilage self-assembly: Neocartilage formation was performed through the self-assembling process as previously described. Briefly, 2% agarose solution was added in a 48-well plate into which a custom-made stainless steel mold with 5 mm diameter cylindrical prongs was immersed. After allowing the agarose to solidify, the well plates were washed with washing medium consisting of DMEM with high glucose/GlutaMAX™ containing 1% P/S/F at least twice prior to cell seeding. Suspended in 100 μl of CDM supplemented with 200 units/ml hyaluronidase type I-S from bovine testes (Sigma Aldrich, St. Louis, Mo.) and 2 μM cytochalasin D (Enzo life Sciences, Farmingdale N.Y.). $2 \times 10^6$ hACs from P3, P5, P7, and P9 with or without rejuvenation were seeded in each well. After 4 hrs of seeding, an additional 400 μl of CDM supplemented with 2 μM cytochalasin D was added to the wells. Medium was exchanged every 24 hrs, and cells were treated with 2 μM cytochalasin D for the first 72 hrs. After neocartilage constructs were unconfined from the agarose wells, medium was exchanged every other day. For the repeated study, cells at P3, P7, and P11 were seeded to form neocartilage constructs as above.

TCL treatment: For the control group, constructs were maintained in CDM. For the TCL-treated group, constructs were maintained in CDM, supplemented with 10 ng/ml TGF-β1 for the full culture duration. At t=7 d, constructs were treated with 2 unit/ml of c-ABC (Sigma Aldrich) for 4 hrs at 37° C., followed by 1 mM zinc sulfate to stop the reaction for 10 min at 37° C. From t=7-21 d, constructs were treated with 0.15 μg/ml of LOXL2 (SignalChem, Richmond, BC, Canada), supplemented with 0.146 mg/ml hydroxylysine and 1.6 μg/ml copper sulfate.

Mechanical testing and biochemical evaluation: Constructs were collected at 5 weeks for mechanical and biochemical evaluation. For compressive mechanical testing, samples were preconditioned with 15 cycles at 5% compressive strain. Incremental stress-relaxation was performed at a strain rate of 1% sample height per second; samples held at 10% strain were allowed to equilibrate, then strained to 20% with collection of force and displacement data. Relaxation modulus ($E_r$), and instantaneous modulus ($E_i$) were calculated using a standard linear solid model. For tensile testing, samples were strained at a constant rate of 1% per second using a TestResource 840L. Young's modulus ($E_Y$) and ultimate tensile strength (UTS) were calculated using a custom MATLAB program. For biochemical assays, wet and dry weights of samples were measured before and after constructs were lyophilized. The lyophilized samples were digested in 125 μg/ml papain (Sigma Aldrich) in 50 mM phosphate buffer containing 2 mM N-acetyl cysteine (Sigma Aldrich), and 2 mM EDTA for 18 hrs at 60° C. GAG content was quantified using a Blyscan Glycosaminoglycan Assay kit (Biocolor, Newtownabbey, Northern Ireland). Total collagen content was assessed using a modified chloramine-T hydroxyproline assay that used hydrochloric acid instead of perchloric acid and a SIRCOL collagen standard (Accurate Chemical and Scientific Corp., Westbury, N.Y.).

Histology and immunohistochemistry: Samples were fixed in 10% neutral-buffered formalin for histological assessment. Fixed samples were paraffin-embedded and sectioned at 5 μm. Sections were stained with hematoxylin and eosin (H&E); safranin-O and fast green; or picrosirius red using standard protocols. Immunohistochemistry (IHC) was used to detect collagen I and II expression using Vectastain ABC and DAB substrate kits (Vector Laboratories, Inc., Burlingame, Calif.). For primary antibodies, rabbit anti-type I collagen at a dilution of 1:500 (Abeam, Cambridge, Mass.) and rabbit anti-type II collagen (Abeam) at a dilution of 1:300 were used to detect type I and II collagen, respectively.

Statistics: All data are shown in mean±SD. Statistical differences among conditions were analyzed using one-way ANOVA with Tukey's post hoc test ($p<0.05$) (JMP12). Statistically significant differences are shown by bars not sharing the same letter.

Results: hAC CCP metrics: The metrics of hAC CCP in monolayer initial seeding density, days in culture, final cell density, expansion factor, doubling time, cumulative expansion factor, and cumulative cell doubling number—are shown in FIG. 3. hACs derived from a 43 year-old, male were passaged up to P8 and the cell expansion factor at each passage ranged from 4.4 to 5.8, with an average of 5.1. In general, with each increasing passage, the growth rate gradually increased, as indicated by decreases in cell doubling time. Passaging to P9 led to a cumulative expansion factor of approximately $1.5 \times 10^6$ and a cell doubling number of 20.6. Cryogenically preserved P2, P4, P6, and P8 hACs underwent one more passage after thawing to be self-assembled into neocartilage: the subsequent doubling time during this additional passage (e.g., to P3, P5, P7, and P9) exhibited a slight decrease, with a range of 1.0 to 1.3, when compared to non-cryogenically preserved cells at respective passages (FIG. 3). For the repeated study, hACs derived from a 34 year-old male were passaged up to P11, leading to a cumulative expansion factor of approximately $12.6 \times 10^6$ and a cell doubling number of 23.6 (FIG. 11).

Figure 4:
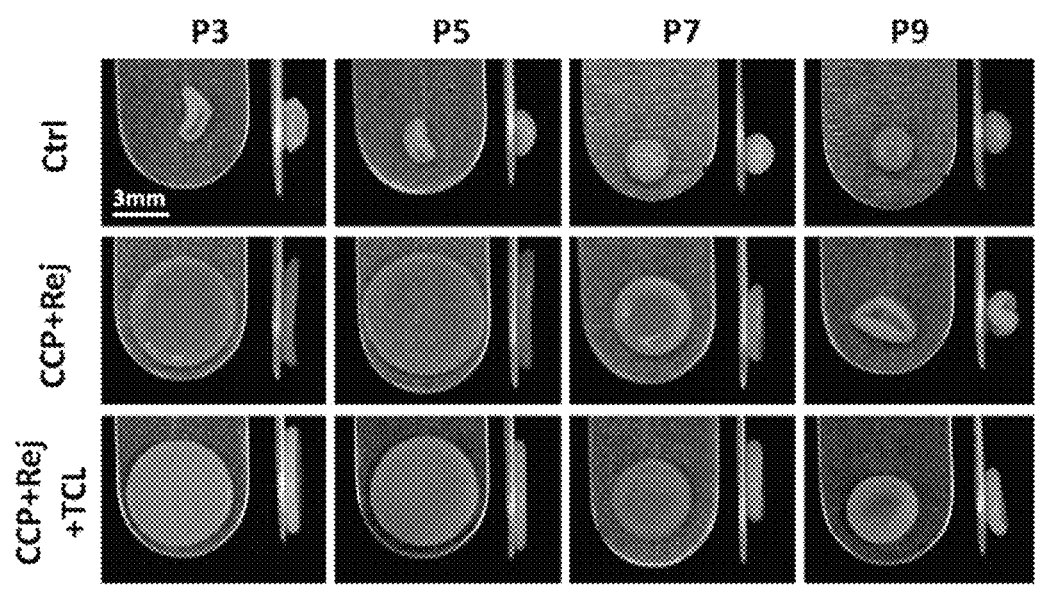
FIG. 4 shows gross morphology of self-assembled human neocartilage (top and side views of hAC neocartilage constructs derived from P3, P5, P7, and P9). The effects of CCP and rejuvenation (CCP+Rej), and CCP and rejuvenation followed by TCL treatment (CCP+Rej+TCL) on hAC neocartilage derived from P3, P5, P7, and P9 (43 yrs, male) are shown. Abbreviations: TCL, TGF-β1+c-ABC+LOXL2. See Example 1.

Gross morphological and histological evaluation of hAC neocartilage: hAC neocartilage exhibited distinctively different gross morphologies at each passage (FIG. 4). P3 and P5 neocartilage constructs were curled at the edges and folded. P7 and P9 hACs formed spherical constructs. In contrast, hAC neocartilage constructs formed by P3, P5, P7, and P9 cells treated with both CCP and rejuvenation were grossly different: treated P3, P5, and P7 hACs self-assembled into flat constructs. With CCP and rejuvenation, P9 constructs were curled and folded, similar to the shapes of P3 and P5 control constructs (FIG. 4).

Figure 12:
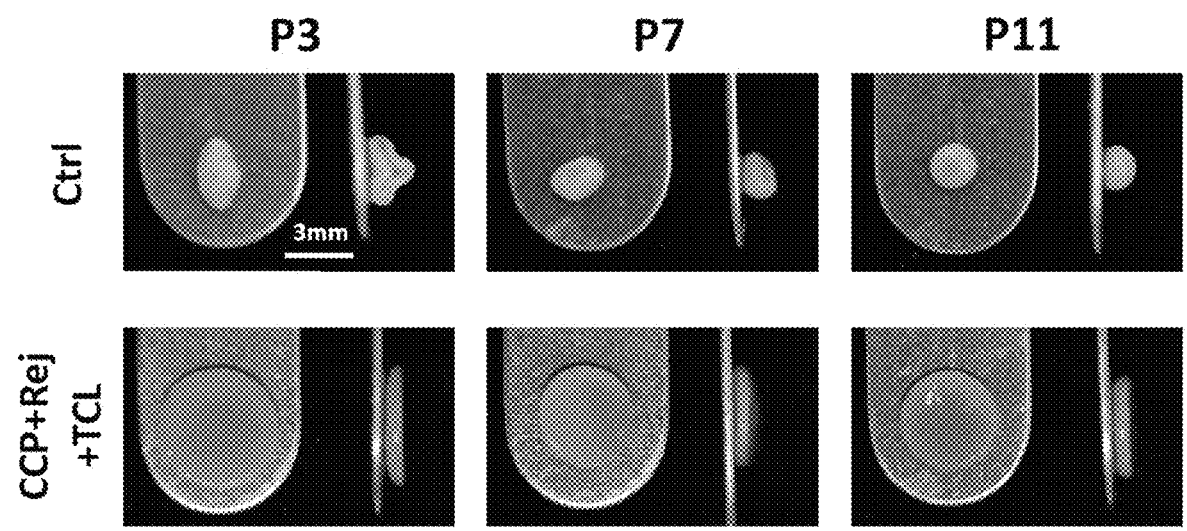
FIG. 12 shows gross morphology of self-assembled human neocartilage (top and side views of hAC neocartilage constructs derived from P3, P7, and P11). The effect of CCP and rejuvenation followed by TCL treatment (CCP+Rej+TCL) on hAC neocartilage derived from P3, P7, and P11 (34 yrs, male) is shown. See Example 1.

Addition of TCL treatment following CCP and rejuvenation yielded more opaque morphologies in P3 and P5 constructs, when compared to constructs without TCL treatment. TCL treatment allowed P7 and P9 hACs to form flat constructs (FIG. 4). Similarly, in a repeated study, TCL treatment following CCP and rejuvenation yielded P7 and P11 hACs, which formed flat constructs (FIG. 12).

Figure 5A:
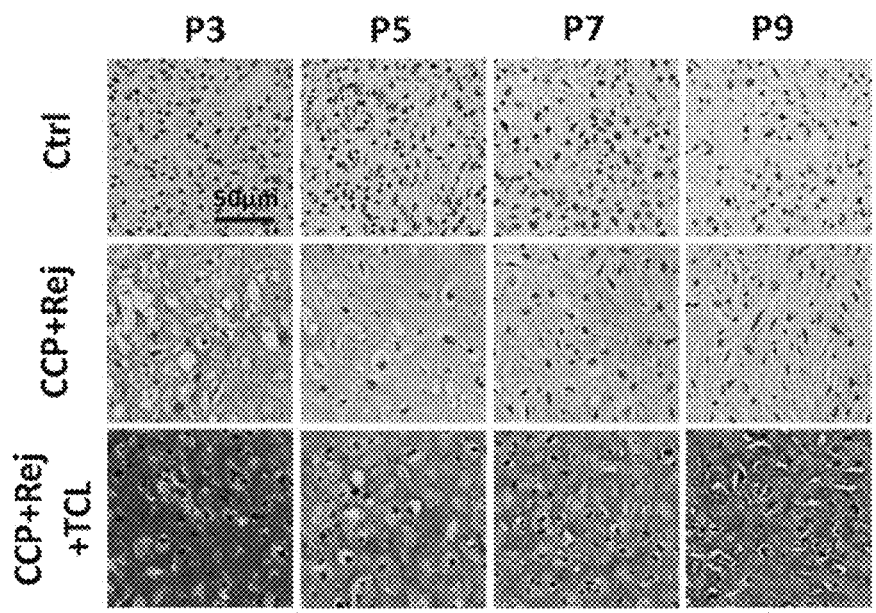
FIG. 5A shows histology of self-assembled human neocartilage with hematoxylin and eosin (H&E) staining. Samples are hAC neocartilage constructs derived from P3, P5, P7, and P9 (43 yrs, male). The effects of CCP and rejuvenation (CCP+Rej), and CCP and rejuvenation followed by TCL treatment (CCP+Rej+TCL) on hAC neocartilage are shown. See Example 1.
Figure 5B:
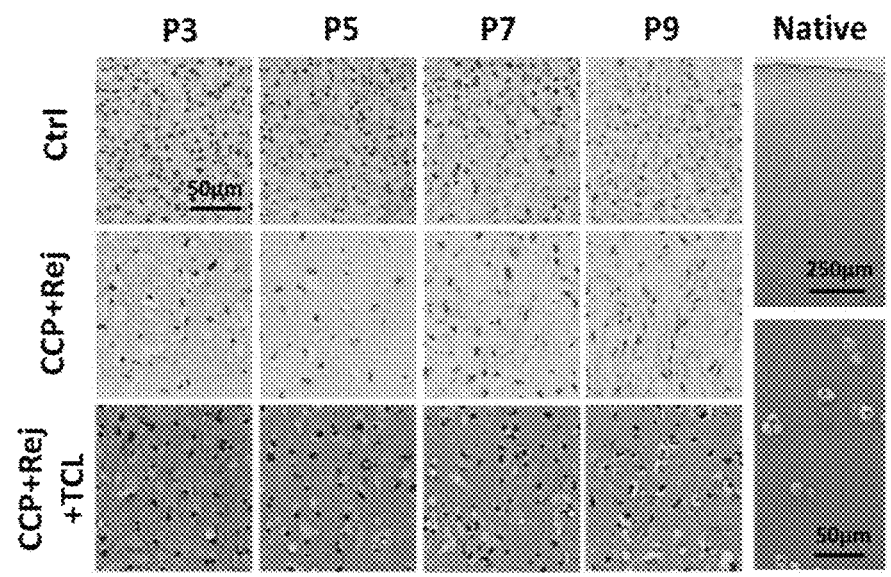
FIG. 5B shows histology of self-assembled human neocartilage with safranin-O staining. Samples are hAC neocartilage constructs derived from P3, P5, P7, and P9 (43 yrs, male). The effects of CCP and rejuvenation (CCP+Rej), and CCP and rejuvenation followed by TCL treatment (CCP+Rej+TCL) on hAC neocartilage are shown. See Example 1.
Figure 6:
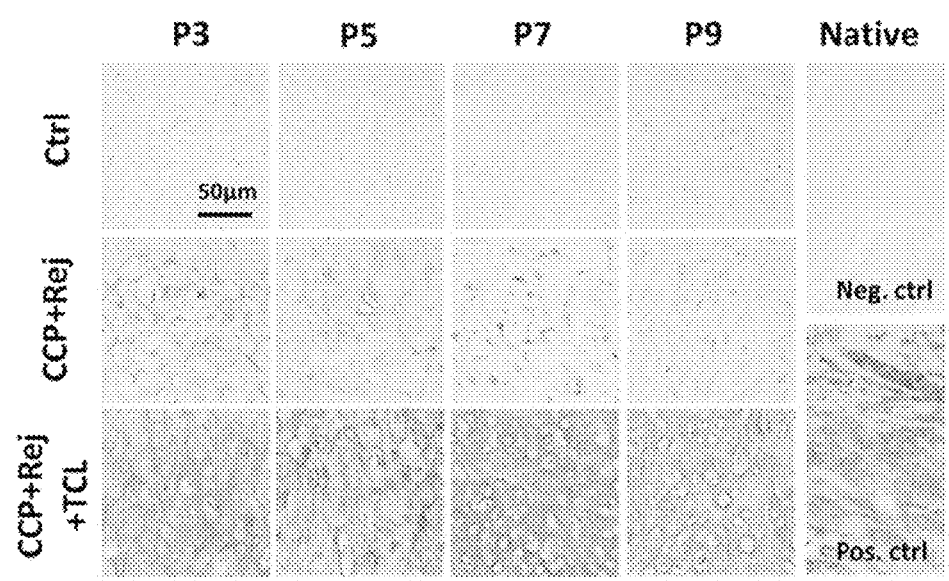
FIG. 6 shows immunohistochemistry for type II collagen in self-assembled human neocartilage. The effects of CCP and rejuvenation (CCP+Rej), and CCP and rejuvenation followed by TCL treatment (CCP+Rej+TCL) on hAC neocartilage derived from P3, P5, P7, and P9 (43 yrs, male) are shown. Nucleus pulposus and annulus fibrosus from human native intervertebral disc were used for positive and negative controls, respectively. See Example 1.
Figure 9:
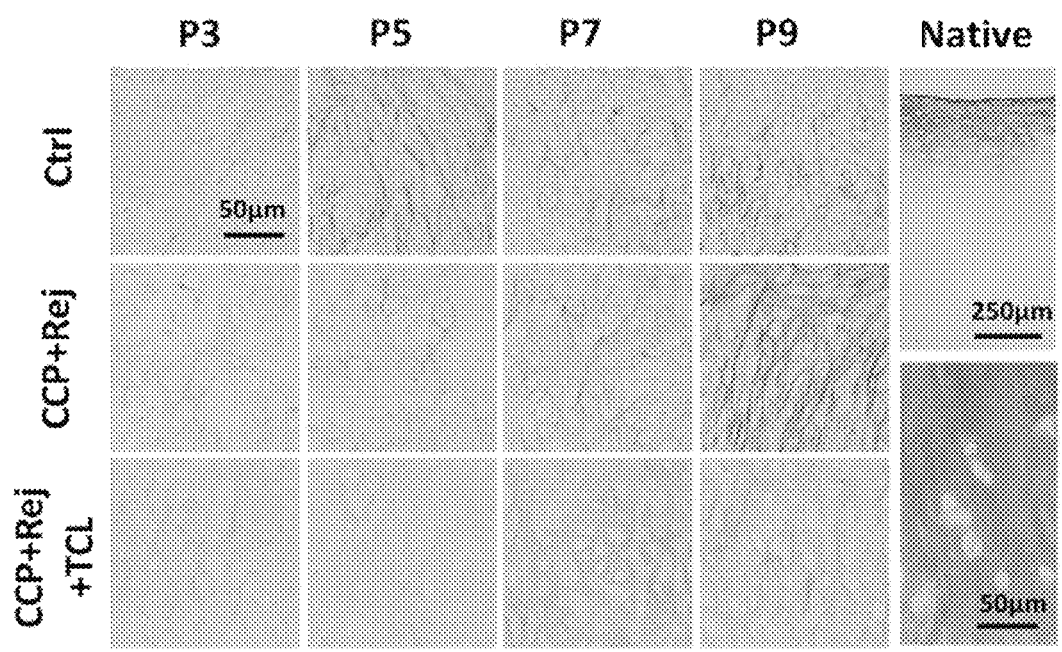
FIG. 9 shows picrosirius red staining of self-assembled human neocartilage. The effects of CCP and rejuvenation (CCP+Rej), and CCP and rejuvenation followed by TCL treatment (CCP+Rej+TCL) on hAC neocartilage constructs derived from P3, P5, P7, and P9 (43 yrs, male) are shown. See Example 1.
Figure 10:
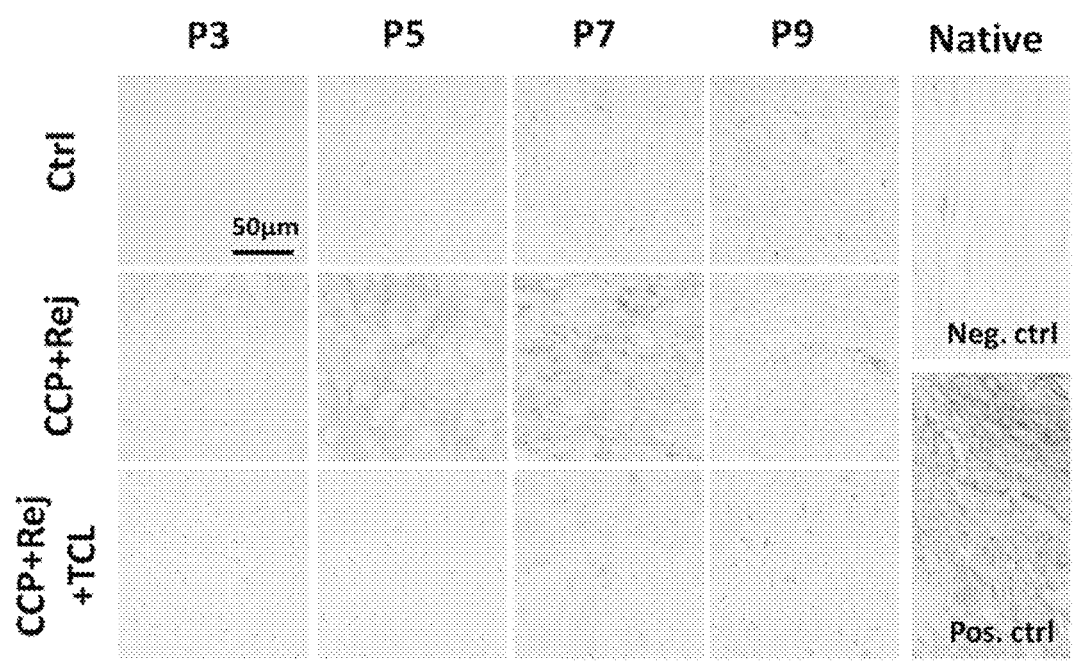
FIG. 10 shows immunohistochemistry for type I collagen in self-assembled human neocartilage. The effects of CCP and rejuvenation (CCP+Rej), and CCP and rejuvenation followed by TCL treatment (CCP+Rej+TCL) on hAC neocartilage derived from P3, P5, P7, and P9 (43 yrs, male) are shown. Annulus fibrosus and nucleus pulposus from human native intervertebral disc were used for positive and negative controls, respectively. See Example 1.
Figure 13:
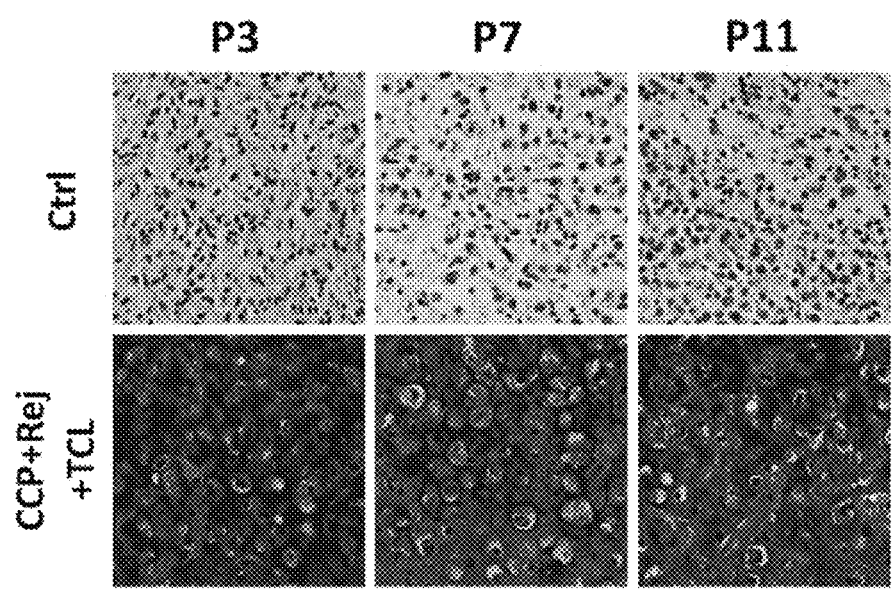
FIG. 13 shows histology of self-assembled human neocartilage with hematoxylin and eosin (H&E) staining. Samples are hAC neocartilage constructs derived from P3, P7, and P11 (34 yrs, male). The effect of CCP and rejuvenation followed by TCL treatment (CCP+Rej+TCL) on hAC neocartilage is shown. See Example 1.

Differences in histological appearance were observed among groups with different passage numbers (FIG. 5, FIG. 5B). Without treatment, hAC neocartilage constructs at any passage number did not display the spherical cell morphology associated with the chondrogenic phenotype (FIG. 5A). With CCP and rejuvenation, P3 and P5 constructs exhibited chondrocytes embedded in lacunae. However, as the passage number increased, presence of lacunae gradually diminished: P9 untreated control constructs barely exhibited lacunae and contained fibroblast-like cells. TCL treatment following CCP and rejuvenation resulted in the presence of spherical cells residing in lacunae for all passages examined (FIG. 5A). Consistent results were shown in the repeated study: constructs derived from all passages (i.e., P3, P7, and P11) contained spherical cells in lacunae (FIG. 13). With CCP and rejuvenation, hAC neocartilage at all passage numbers were positive for safranin-O and showed significantly more intense staining compared to control neocartilage (FIG. 5B). However, the intensity of staining decreased as the passage number increased. TCL treatment following CCP and rejuvenation further enhanced the intensity of this stain, though the intensities between P3 and P5 constructs were comparable, and, to some extent, the intensity decreased in P7 and P9 constructs. CCP and rejuvenation treatment significantly increased the presence of type II collagen over control neocartilage at all passages, though staining intensity decreased as the passage number increased (FIG. 6). With TCL treatment, hAC neocartilage at all passages showed significantly more intense staining of type II collagen. Interestingly, with CCP and rejuvenation, more intense type I collagen was observed in P5 and P7 constructs compared to P3 and P9 constructs (FIG. 9). TCL-treated P3 and P5 constructs were negative for type I collagen staining, and TCL-treated P7 and P9 constructs exhibited minimal staining for this protein.

Figure 7A:
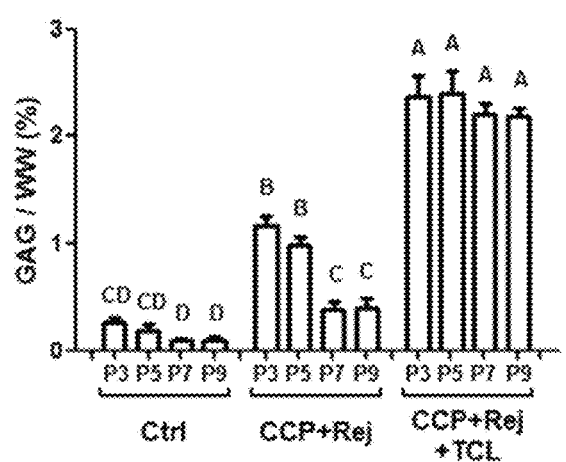
FIG. 7A shows glycosaminoglycan (GAG) content in hAC neocartilage constructs normalized by wet weight (WW). The effects of CCP and rejuvenation (CCP+Rej), and CCP and rejuvenation followed by TCL treatment (CCP+Rej+TCL) on hAC neocartilage derived from P3, P5, P7, and P9 (43 yrs, male) are shown. See Example 1.
Figure 7B:
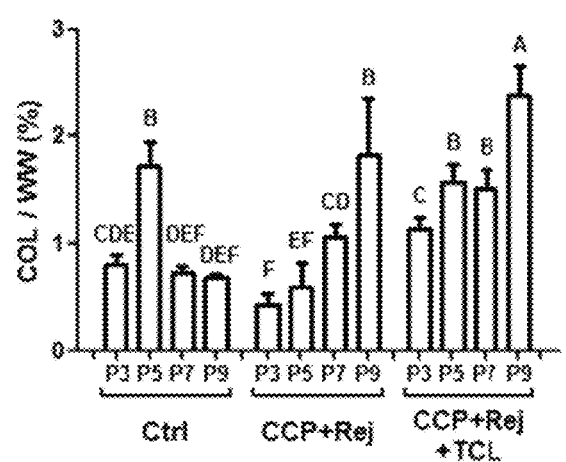
FIG. 7B shows total collagen (COL) content in hAC neocartilage constructs normalized by wet weight (WW). The effects of CCP and rejuvenation (CCP+Rej), and CCP and rejuvenation followed by TCL treatment (CCP+Rej+TCL) on hAC neocartilage derived from P3, P5, P7, and P9 (43 yrs, male) are shown. See Example 1.
Figure 14A:
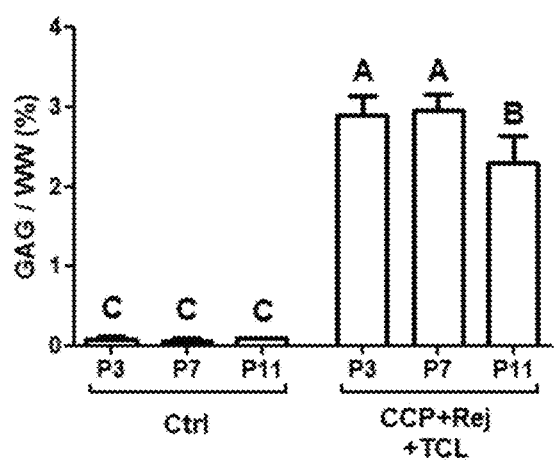
FIG. 14A shows glycosaminoglycan (GAG) content in hAC neocartilage constructs normalized by wet weight (WW). The effect of CCP and rejuvenation followed by TCL treatment (CCP+Rej+TCL) on hAC neocartilage derived from P3, P7, and P11 (34 yrs, male) is shown. See Example 1.
Figure 14B:
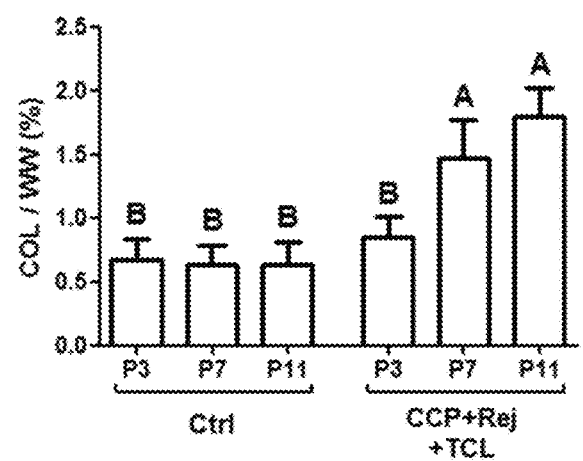
FIG. 14B shows total collagen (COL) content in hAC neocartilage constructs normalized by wet weight (WW). The effect of CCP and rejuvenation followed by TCL treatment (CCP+Rej+TCL) on hAC neocartilage derived from P3, P7, and P11 (34 yrs, male) is shown. See Example 1.
Figure 15A:
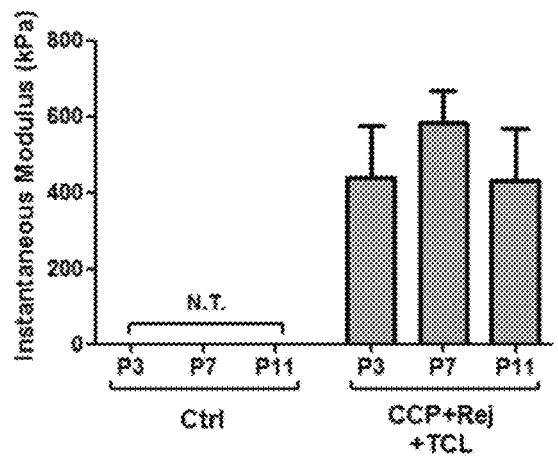
FIG. 15A shows instantaneous modulus of hAC neocartilage constructs as a means of measuring compressive properties of self-assembled human neocartilage. The effect of CCP and rejuvenation followed by TCL treatment (CCP+Rej+TCL) on hAC neocartilage derived from P3, P7, and P11 (34 yrs, male) is shown. See Example 1.
Figure 15B:
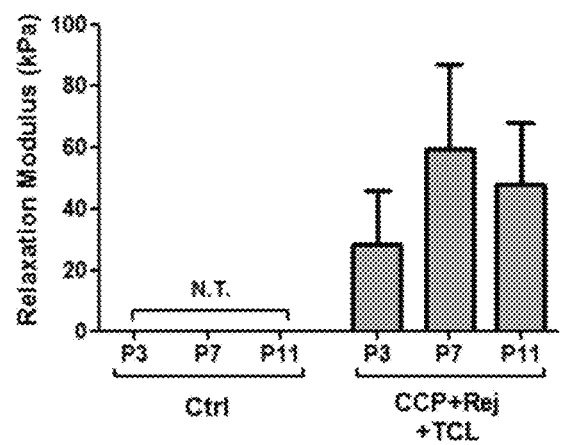
FIG. 15B shows relaxation modulus of hAC neocartilage constructs as a means of measuring compressive properties of self-assembled human neocartilage. The effect of CCP and rejuvenation followed by TCL treatment (CCP+Rej+TCL) on hAC neocartilage derived from P3, P7, and P11 (34 yrs, male) is shown. See Example 1.
Figure 15C:
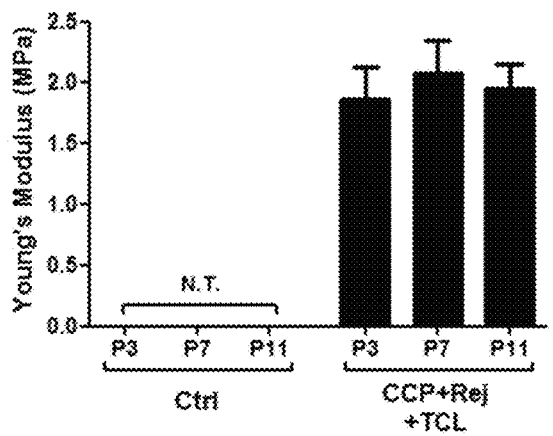
FIG. 15C shows Young's modulus of hAC neocartilage constructs as a means of measuring tensile properties of self-assembled human neocartilage. The effect of CCP and rejuvenation followed by TCL treatment (CCP+Rej+TCL) on hAC neocartilage derived from P3, P7, and P11 (34 yrs, male) is shown. See Example 1.
Figure 15D:
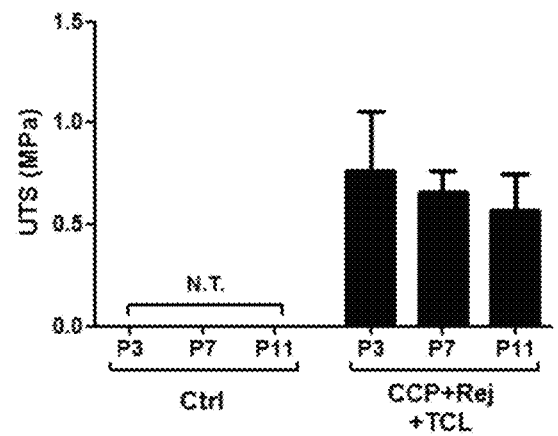
FIG. 15D shows UTS of hAC neocartilage constructs as a means of measuring tensile properties of self-assembled human neocartilage. The effect of CCP and rejuvenation followed by TCL treatment (CCP+Rej+TCL) on hAC neocartilage derived from P3, P7, and P11 (34 yrs, male) is shown. See Example 1.

Biochemical and mechanical properties of hAC neocartilage: treatment with CCP and rejuvenation, with or without being followed by TCL treatment, exhibited a range of enhancement in biochemical and mechanical properties of hAC neocartilage at different passages (FIGS. 7A-B and FIG. 8A-D). Without treatment, GAG content normalized by wet weight (GAG/WW) in hAC neocartilage tended to decrease as the passage number increased (FIG. 7A). For the CCP and rejuvenation group, GAG/WW in hAC neocartilage at each passage significantly increased by 3- to 4-fold when compared to that in control neocartilage. Addition of TCL treatment further increased GAG/WW in hAC neocartilage at each passage by 1 to 4.5-fold, compared to hAC neocartilage without TCL treatment. With added TCL treatment, P7 and P9 constructs produced GAG contents similar to P3 and P5 constructs. Interestingly, total collagen content per wet weight (COL/WW) was the highest in P5 constructs compared to hAC neocartilage constructs at other passages (FIG. 7B). Although COL/WW in control P3 and P5 constructs was significantly decreased with CCP and rejuvenation by 50% and 65%, respectively, P7 and P9 constructs contained increased COL/WW by 57% and 157%, respectively, over control neocartilage. COL/WW was further increased in hAC neocartilage at each passage with TCL treatment by 0.3 to 1.8-fold when compared to hAC neocartilage formed using cells that had undergone CCP and rejuvenation, but without TCL treatment. Similar results were shown in the repeated study, which examined cells up to P11 (FIGS. 14A and 14B).

Figure 8A:
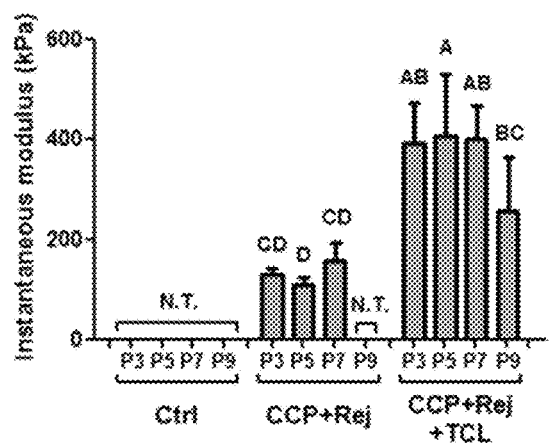
FIG. 8A shows instantaneous modulus of hAC neocartilage constructs as a means of measuring compressive properties of self-assembled human neocartilage. The effects of CCP and rejuvenation (CCP+Rej), and CCP and rejuvenation followed by TCL treatment (CCP+Rej+TCL) on hAC neocartilage derived from P3, P5, P7, and P9 (43 yrs, male) are shown. See Example 1.
Figure 8B:
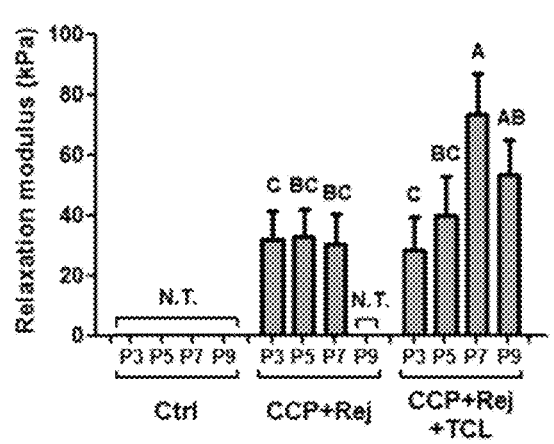
FIG. 8B shows relaxation modulus of hAC neocartilage constructs as a means of measuring compressive properties of self-assembled human neocartilage. The effects of CCP and rejuvenation (CCP+Rej), and CCP and rejuvenation followed by TCL treatment (CCP+Rej+TCL) on hAC neocartilage derived from P3, P5, P7, and P9 (43 yrs, male) are shown. See Example 1.
Figure 8C:
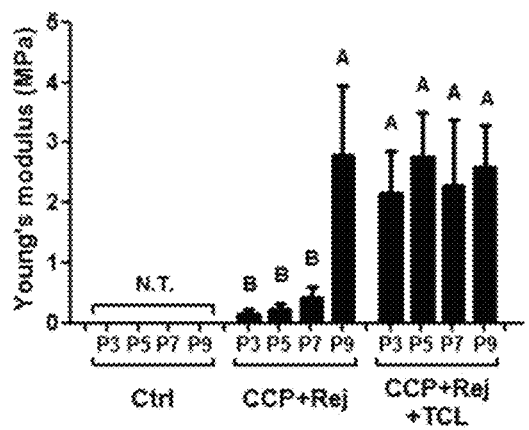
FIG. 8C shows Young's modulus of hAC neocartilage constructs as a means of measuring tensile properties of self-assembled human neocartilage. The effects of CCP and rejuvenation (CCP+Rej), and CCP and rejuvenation followed by TCL treatment (CCP+Rej+TCL) on hAC neocartilage derived from P3, P5, P7, and P9 (43 yrs, male) are shown. See Example 1.
Figure 8D:
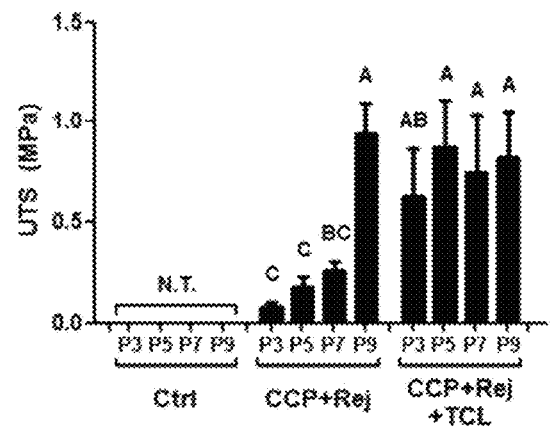
FIG. 8D shows UTS of hAC neocartilage constructs as a means of measuring tensile properties of self-assembled human neocartilage. The effects of CCP and rejuvenation (CCP+Rej), and CCP and rejuvenation followed by TCL treatment (CCP+Rej+TCL) on hAC neocartilage derived from P3, P5, P7, and P9 (43 yrs, male) are shown. See Example 1.

Mechanically, control hAC neocartilage constructs were not testable for compression and tension at any passage (FIG. 8A-D). With CCP and rejuvenation, P3, P5, and P7 constructs demonstrated similar compressive relaxation modulus and instantaneous modulus values, while P9 constructs were not evaluated in compression due to their shape (FIG. 8A and FIG. 8B). With addition of TCL treatment, the relaxation modulus value of P7 constructs was significantly increased by 1.4-fold when compared to P7 constructs with CCP and rejuvenation treatment only. Compressive instantaneous modulus was significantly increased with TCL treatment in neocartilage at P3, P5, and P7, by 1.5 to 2.7-fold when compared to neocartilage with CCP and rejuvenation only. The compressive properties appeared to be similar regardless of passage number among the TCL-treated constructs. With CCP and rejuvenation, tensile stiffness and strength exhibited comparable values among P3, P5, and P7 constructs, whereas P9 constructs demonstrated significantly enhanced tensile properties when compared to constructs from other passages (FIG. 8C and FIG. 8D). Addition of TCL treatment significantly increased tensile stiffness in hAC neocartilage at P3, P5, and P7 by 20.0-fold, 12.5-fold, and 4.8-fold, respectively, and tensile strength by 5.0-fold, 3.5-fold, and 1.3-fold, respectively, when compared to CCP and rejuvenation treatment only. Tensile properties in TCL-treated P9 constructs were comparable to the properties in P9 constructs with CCP and rejuvenation treatment only. No significant difference in tensile properties was observed among TCL-treated hAC neocartilage. In a repeated study, CCP and rejuvenation followed by TCL treatment allowed constructs from all passages (i.e., P3, P7, and P11) to exhibit similar compressive and tensile properties (FIG. 15)

Example 1 shows that TCL treatment, applied to neocartilage formed using cells that had undergone CCP and rejuvenation, can be used to enhance functional properties of hAC neocartilage with high passage numbers. CCP and rejuvenation treatment elicited significant changes in construct and cell morphologies, exhibiting flattened constructs up to P7 with chondrogenic phenotype present. The addition of TCL treatment following CCP and rejuvenation generated P9 constructs with flat construct morphology and cells in lacunae. Notably, at P7 and P9, TCL treatment yielded human neocartilage with functional properties similar to those derived from P3 and P5 cells, as demonstrated by GAG and type II collagen staining, and by compressive and tensile properties. In the repeated study, CCP and rejuvenation followed by TCL treatment generated P11 constructs with flat construct morphology and cells in lacunae. Furthermore, the P11 constructs displayed similar biochemical and mechanical properties as constructs derived from P3 and P7 cells. Even with extensive passages, a combination of CCP, rejuvenation, and TCL treatment yielded neocartilage with functional properties similar to those of neocartilage derived from low passages.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method of preparing human cartilage cells, expanded to passages N=5 (P5) or beyond, that are functional for neocartilage production, said method comprising:

(a) culturing a population of human cartilage cells at passage 0 (P0) in monolayer in a medium comprising two or more of: a transforming growth factor (TGF)-β superfamily protein, a fibroblast growth factor, and a mitogen; and expanding said cells to passage 5 (P5) or beyond in said medium;

(b) subjecting the expanded human cartilage cells from (a) to dissociation and subsequent culture in a three-dimensional environment in a medium comprising two or more of: a transforming growth factor (TGF)-β superfamily protein, a growth differentiation factor, and a bone morphogenetic protein; and (c) subjecting the human cartilage cells from (b) to a medium comprising: a transforming growth factor (TGF)-β superfamily protein, a proteoglycan and/or glycosaminoglycan degrading agent, and a cross-linking agent; wherein the human cartilage cells from (c) retain a phenotype that is similar to or better than the phenotype exhibited by the human cartilage cells formed by cartilage cells at P0 (native state) or at passage N-X, wherein N is the passage number, X is any integer between 1 and N.

2. The method of claim 1 further comprising dissociating cells from (b) prior to (c).

3. The method of claim 1, wherein culturing cells according to (a), (b), or both (a) and (b) further comprises subjecting the cells to mechanical stimulation.

4. The method of claim 3, wherein the mechanical stimulation comprises fluid induced shear stress, hydrostatic pressure, compression, tension, or a combination thereof.

5. The method of claim 1, wherein the method further comprises using the cells from (c) to treat chondral lesions, osteochondral lesions, and osteoarthritic conditions.

6. The method of claim 1, wherein the cells in (a) are derived from musculoskeletal tissue, adult stem cells, embryonic stem cells, genetically modified cells, or a combination thereof.

7. The method of claim 1, wherein the medium in (a) further comprises one or more of epidermal growth factor (EGF), insulin-like growth factor (IGF), superficial zone protein (SZP)/proteoglycan 4 (PRG4), proteoglycan molecules, collagen molecules, matrix degrading enzymes, cytoskeleton modifying reagents, cross-linking agents, or a combination thereof.

8. The method of claim 1, wherein the medium in (b) further comprises one or more of epidermal growth factor (EGF), fibroblast growth factor (FGF), insulin-like growth factor (IGF), superficial zone protein (SZP)/proteoglycan 4 (PRG4), proteoglycan molecules, collagen molecules, matrix degrading enzymes, cytoskeleton modifying reagents, cross-linking agents, or a combination thereof.

9. The method of claim 1, wherein the medium in (c) further comprises one or more of fibroblast growth factor 2 (FGF-2), epidermal growth factor (EGF), insulin-like growth factor (IGF), superficial zone protein (SZP)/proteoglycan 4 (PRG4), proteoglycan molecules, collagen molecules, cytoskeleton modifying reagents, or a combination thereof.

10. The method of claim 1, wherein culturing cells according to (a), (b), or both (a) and (b) comprises subjecting the cells to hypoxic conditions to reach the effects of culturing cells in less than 21% oxygen, subjecting the cells to a chemical treatment with one or more of desferrioxamine, cobalt, glucose oxidase (GOX)/catalase (CAT), or a combination thereof, or subjecting the cells to both the hypoxic conditions and chemical treatment.

11. The method of claim 1, wherein the method further comprises culturing the cells in (c) in a three-dimensional culture.

12. The method of claim 11, wherein the three-dimensional culture comprises a scaffold-free three-dimensional culture or a scaffold-based three-dimensional culture.

13. The method of claim 11, wherein the cells in the three-dimensional culture are subjected to mechanical stimulation, including fluid induced shear stress, compressive stress, tensile stress, hydrostatic pressure, or a combination thereof.

14. The method of claim 11, wherein the cells in the three-dimensional culture are subjected to hypoxic conditions to reach the effects of culturing cells in less than 21% oxygen, to a chemical treatment with one or more of desferrioxamine, cobalt, glucose oxidase (GOX)/catalase (CAT), or a combination thereof, or to both the hypoxic conditions and chemical treatment.

15. A method of preparing human cartilage cells having a phenotype that is similar or better than a phenotype exhibited by cartilage cells at P0 (native state) or at passage N-X, wherein N is the passage number, X is any integer between 1 and N, said method comprising:

(a) culturing a population of human cartilage cells at passage 0 (P0) in monolayer in a medium comprising two or more of: a transforming growth factor (TGF)-β superfamily protein, a fibroblast growth factor, and a mitogen; and expanding said cells to passage 5 (P5) or beyond in said medium;

(b) subjecting the expanded human cartilage cells from (a) to dissociation and subsequent culture in a three-dimensional environment in a medium comprising two or more of: a transforming growth factor (TGF)-β superfamily protein, a growth differentiation factor, and a bone morphogenetic protein;

(c) subjecting the human cartilage cells from (b) to a medium comprising a transforming growth factor (TGF)-β superfamily protein, a proteoglycan and/or glycosaminoglycan degrading agent, and a cross-linking agent; and (d) comparing a phenotype of the human cartilage cells in (c) to a phenotype of human cartilage cells at an earlier passage or P0 from (a), wherein the phenotype of the human cartilage cells from (c) is similar to or better than the phenotype exhibited by cartilage cells at P0 (native state) or at passage N-X, wherein N is the passage number, X is any integer between 1 and N;

wherein the cells are functional for neocartilage production.

16. The method of claim 15 further comprising culturing cells in (c) in a three-dimensional culture.

17. The method of claim 16, wherein the three-dimensional culture comprises a scaffold-free three-dimensional culture or a scaffold-based three-dimensional culture.

18. A method comprising:

(a) culturing a population of human cartilage cells at passage 0 (P0) in monolayer in a medium comprising two or more of: a transforming growth factor (TGF)-β superfamily protein, a fibroblast growth factor, and a mitogen; and expanding said cells to passage 5 (P5) or beyond in said medium;

(b) subjecting the expanded human cartilage cells from (a) to dissociation and subsequent culture in a three-dimensional environment in a medium comprising two or more of: a transforming growth factor (TGF)-β superfamily protein, a growth differentiation factor, and a bone morphogenetic protein; and (c) subjecting the cells from (b) to a medium comprising:
a transforming growth factor (TGF)-β superfamily protein, a proteoglycan and/or glycosaminoglycan degrading agent, and a cross-linking agent;
wherein the cells in (c) are functional for neocartilage production.

19. The method of claim 18 further comprising dissociating cells from (b) prior to (c).

20. The method of claim 18 further comprising culturing cells in (c) in a three-dimensional culture.

* * * * *